(12) United States Patent
Belfadhel et al.

(10) Patent No.: US 7,977,447 B2
(45) Date of Patent: Jul. 12, 2011

(54) METHOD FOR MAKING CARBONATES AND ESTERS

(75) Inventors: Hatem Abdallah Belfadhel, Roosendaal (NL); Hans-Peter Brack, Herrliberg (CH); Ricardo Godoy-Lopez, Terneuzen (NL); Dennis James Patrick Maria Willemse, Standdaarbuiten (NL)

(73) Assignee: Sabic Innovative Plastics IP B.V. (NL)

( * ) Notice: Subject to any disclaimer, the term of this patent is extended or adjusted under 35 U.S.C. 154(b) by 0 days.

(21) Appl. No.: 12/343,867

(22) Filed: Dec. 24, 2008

(65) Prior Publication Data

US 2010/0123097 A1 May 20, 2010

Related U.S. Application Data

(60) Provisional application No. 61/115,678, filed on Nov. 18, 2008.

(51) Int. Cl.
*C08G 64/00* (2006.01)
*C08G 63/02* (2006.01)

(52) U.S. Cl. ......... 528/196; 524/451; 528/198; 568/451

(58) Field of Classification Search .................. 524/451; 528/196, 198; 568/451
See application file for complete search history.

(56) References Cited

U.S. PATENT DOCUMENTS

| | | | |
|---|---|---|---|
| 2,399,118 A | 4/1946 | Homeyer et al. | |
| 2,437,388 A | 3/1948 | Homeyer et al. | |
| 3,131,197 A | 4/1964 | Swintosky et al. | |
| 3,155,683 A * | 11/1964 | Moody | 549/228 |
| 3,738,963 A * | 6/1973 | Praetorius | 528/206 |
| 4,323,668 A | 4/1982 | Brunelle | |
| 4,344,881 A | 8/1982 | Strege et al. | |
| 4,705,799 A | 11/1987 | Gregory | |
| 4,705,820 A | 11/1987 | Wang et al. | |
| 4,863,999 A | 9/1989 | MacLeay et al. | |
| 6,323,302 B1 | 11/2001 | Sasaki et al. | |
| 6,410,777 B1 | 6/2002 | Kaneko et al. | |
| 6,420,512 B1 | 7/2002 | McCloskey et al. | |
| 6,420,513 B2 | 7/2002 | Minami | |
| 6,448,365 B1 | 9/2002 | Funakoshi et al. | |
| 6,506,871 B1 | 1/2003 | Silvi et al. | |
| 6,518,391 B1 | 2/2003 | McCloskey et al. | |
| 6,548,623 B2 | 4/2003 | Brunelle et al. | |
| 6,747,119 B2 | 6/2004 | Brack et al. | |
| 6,790,929 B2 | 9/2004 | Silvi et al. | |
| 7,132,499 B2 * | 11/2006 | Tobita et al. | 528/272 |
| 2003/0139529 A1 | 7/2003 | O'Neil et al. | |
| 2003/0149223 A1 | 8/2003 | McCloskey et al. | |
| 2004/0068086 A1 | 4/2004 | Day et al. | |
| 2006/0025622 A1 | 2/2006 | Buckley et al. | |
| 2006/0069228 A1 | 3/2006 | McCloskey et al. | |
| 2007/0282091 A1 | 12/2007 | Buckley et al. | |
| 2008/0004379 A1 | 1/2008 | Berndsen et al. | |
| 2008/0287640 A1 | 11/2008 | Belfadhel et al. | |

FOREIGN PATENT DOCUMENTS

| | | |
|---|---|---|
| DE | 883902 | 7/1953 |
| DE | 2950069 A1 | 7/1980 |
| EP | 0474342 A1 | 3/1992 |
| EP | 0764673 A2 | 3/1997 |
| EP | 0844233 A1 | 5/1998 |
| EP | 0980861 A1 | 2/2000 |
| EP | 0992522 A1 | 4/2000 |
| EP | 11147841 A1 | 7/2001 |
| FR | 2154524 A1 | 5/1973 |
| GB | 995475 A | 6/1965 |
| GB | 2074561 A | 11/1981 |
| JP | 2000129112 | 5/2000 |
| JP | 2005239602 A | 9/2005 |
| WO | 91/10004 | 7/1991 |
| WO | 2009155592 A1 | 12/2009 |

OTHER PUBLICATIONS

Dyen et al., 2-Oxazolidones, Chemical Reviews, Apr. 1967, vol. 67(2), pp. 197-246.
Bayer AG, Liquides hydrauliques du type esters d'acide carbonique, May 11, 1973, Machine translation in English of FR 2154524 retrieved from espacenet.
General Electric, Method to the preparation of mono carbonates, Jul. 3, 1980, Machine translation in English of DE 2950069 retrieved from espacenet.
Japanese Patent No. 2000129112 (A); Publication Date: May 9, 2000; Abstract Only; 1 Page.
International Search Report; International Application No. PCT/US2009/060849; International Filing Date: Oct. 15, 2009; Date of Mailing: May 25, 2010; 10 Pages.
Written Opinion of the International Searching Authority; International Application No. PCT/US2009/060849; International Filing Date: Oct. 15, 2009; Date of Mailing: May 25, 2010; 14 Pages.

* cited by examiner

*Primary Examiner* — Terressa M Boykin
(74) *Attorney, Agent, or Firm* — Cantor Colburn LLP

(57) ABSTRACT

A method for forming a monomeric carbonate includes the step of combining a monofunctional alcohol or a difunctional diol with an ester-substituted diaryl carbonate to form a reaction mixture. Similarly, a method for forming a monomeric ester includes the step of combining a monofunctional carboxylic acid or ester with an ester-substituted diaryl carbonate to form a reaction mixture. These methods further include the step of allowing the reaction mixtures to react to form a monomeric carbonate or a monomeric ester, respectively.

26 Claims, 18 Drawing Sheets

Example 1: Synthesis of di-PCP Carbonate

Mass Spectra for Example 1

Example 2: Synthesis of monocapped PCP carbonate

Gas Chromatogram for Example 2

Synthesis of 1,3-dioxolan-2-one

Fig. 7 Synthesis of 1,3-benzodioxol-2-one

Synthesis of 1,3-dioxan-2-one

Synthesis of 4H-1, 3-benzodioxin-2-one

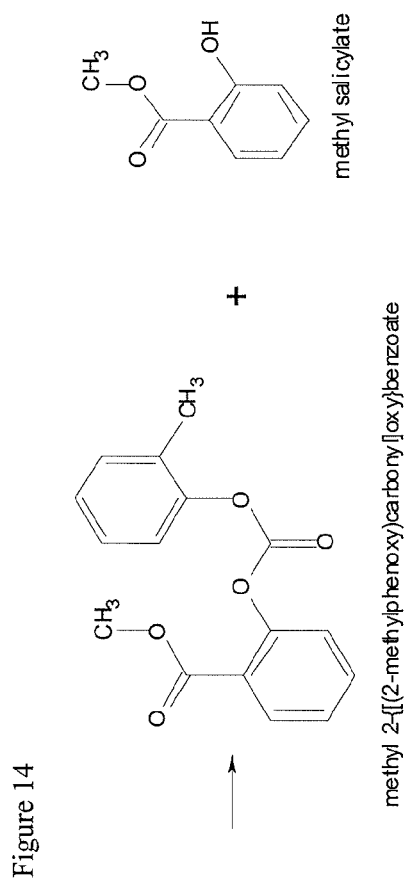
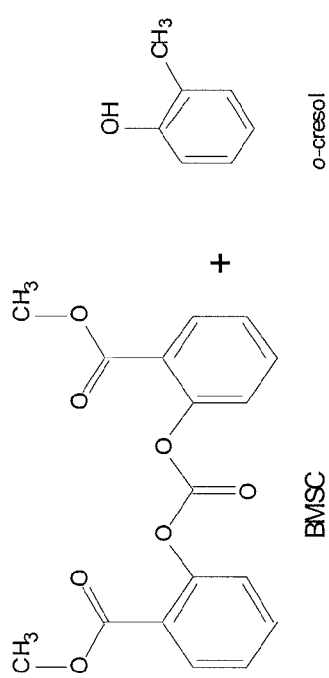
Figure 14

METHOD FOR MAKING CARBONATES AND ESTERS

RELATED APPLICATIONS

The present application is a non-provisional application of U.S. Provisional Patent Application Ser. No. 61/115,678 filed on Nov. 18, 2008, which is incorporated herein by reference for all purposes.

BACKGROUND OF THE INVENTION

This application relates to the preparation of symmetric and asymmetric linear and cyclic monomeric carbonates and esters using ester-substituted diaryl carbonates such as bismethyl salicyl carbonate as a reactant.

Carbonates and esters play an important role as intermediate products for numerous syntheses and as products for special fields of use including agricultural chemistry and/or medicinal chemistry, among others. Linear carbonates and cyclic aliphatic carbonates are used in the formulation of flavors and fragrances. Carbonates are also used as extractants, plasticizers, spinning dopes for synthetic fibers, electrolytes, and additives for cleansing agents. Esters are also used in agricultural chemistry and/or medicinal chemistry, and esters also find application as plasticizers, UV absorbers and light stabilizers, anti-microbials, surfactants, food additives, fragrance agents, fixatives, insect repellants, dye carriers.

Monomeric carbonates are commonly synthesized by reactions making use of phosgene gas or a solid phosgene precursor such as triphosgene in a reaction with one or two alcohols or in the case of a cyclic carbonates with diols. The adoption of triphosgene is preferred for safety reasons, even though it costs more and is generally less reactive, requiring longer reactions at higher temperatures. However, triphosgene is only "safe" relative to phosgene itself and it is still classified as a very hazardous material that can generate hazardous decomposition products namely hydrogen chloride, chlorine, phosgene in addition to the carbon monoxide as well as carbon dioxide normally resulting from the extreme thermal degradation of organic compounds. Carbonates can also be made from reaction of a carbon dioxide with an alcohols or diols under pressure and in the presence of catalysts.

Monomeric esters can be synthesized by numerous reactive processes including esterification reactions between an alcohol and an acid and transesterification reactions between two esters. The carbonate and ester forming reactions often require long reactions times and/or high temperatures, and/or catalyst to achieve high conversion to desired product.

SUMMARY OF THE INVENTION

The present invention provides methods for the synthesis of monomeric carbonates through the reaction of alcohols or diols with an ester-substituted diaryl carbonate, such as bismethyl salicyl carbonate (BMSC) with or without the use of catalyst. The present invention also provides methods for the synthesis of monomeric esters through the reaction of ester-substituted diaryl carbonate with an acid or an ester and optionally an alcohol with or without the use of catalyst. The reactions can be carried out at low temperatures, for example at room temperature, (or high temperatures if so desired) to provide high yields of the product in relatively short periods of time. Furthermore, the breakdown products of BMSC are methyl salicylate and salicylic acid, both of which at low concentrations are accepted ingredients in foods and pharmaceuticals.

In one embodiment, the present invention provides a method of forming a linear symmetric or asymmetric monomeric carbonate compound of the formula:

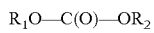

wherein $R_1$ and $R_2$ are the same or different and are each independently selected from the group consisting of optionally-substituted linear or branched alkyl, alkene, cycloalkyl, cycloalkenyl, aryl, heteroatom-containing aryl, and aralkyl groups. In the present embodiment the linear (e.g. non-cyclic) monomeric carbonate is formed by reacting a compound of structure HO—$R_1$ and a compound of structure $R_2$—OH with an ester-substituted diaryl carbonate to form the monomeric carbonate compound. In specific embodiments, the ester-substituted diaryl carbonate is BMSC.

In another embodiment the present invention provides a method of forming a monomeric carbonate compound of the formula:

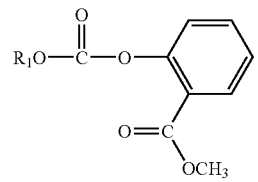

wherein $R_1$ described above. The method comprising reacting $HOR_1$ with bismethyl salicyl carbonate to form the compound.

In another embodiment the present invention provides a method of forming a cyclic monomeric carbonate compound of the formula:

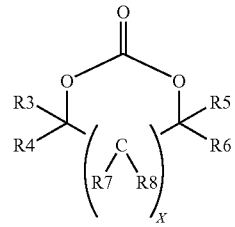

wherein X is 0 or 1, $R_3$, $R_4$, $R_5$, and $R_6$ are the same or different and are each independently selected from the group consisting of hydrogen, optionally-substituted linear or branched alkyl, alkene, cycloalkyl, cycloalkenyl, aryl, heteroatom-containing aryl, and aralkyl groups, or $R_3$ or $R_4$ in combination with $R_5$ or $R_6$ forms a ring structure (e.g. a five or six-member ring). When x=0, combinations of $R_3$ or $R_4$ and $R_5$ or $R_6$ may also be absent to form a double bond, and $R_7$ and $R_8$ when x is 1 are the same or different and are each independently selected from the group consisting of hydrogen, optionally-substituted linear or branched alkyl, alkene, cycloalkyl, cycloalkenyl, aryl, heteroatom-containing aryl, and aralkyl groups. Combinations of $R_7$ or $R_8$ with $R_3$, $R_4$, $R_5$, or $R_6$ may also be absent to form a double bond.

In another embodiment, the present invention provides a method of forming an activated ester compound of the formula:

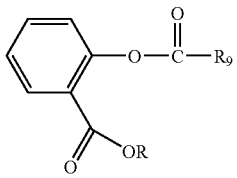

wherein R is an alkyl group, phenyl group, or a benzyl group, and $R_9$ is selected from the group consisting of optionally-substituted linear or branched alkyl, alkene, cycloalkyl, cycloalkenyl, aryl, heteroatom-containing aryl, and aralkyl groups, said method comprising reacting an ester-substituted diaryl carbonate with a compound of the formula:

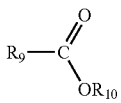

wherein $R_9$ is described above and $R_{10}$ is selected from the group consisting of hydrogen, and optionally-substituted linear or branched alkyl, alkene, cycloalkyl, cycloalkenyl, aryl, heteroatom-containing aryl, and aralkyl groups, thereby forming the compound.

In another embodiment, the present invention provides a method of forming a monomeric ester compound of the formula:

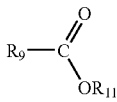

wherein $R_9$ and $R_{11}$ are the same or different and each are independently selected from the group consisting of optionally-substituted linear or branched alkyl, alkene, cycloalkyl, cycloalkenyl, aryl, heteroatom-containing aryl, and aralkyl groups, said method comprising reacting an ester-substituted diaryl carbonate with a compound of the formula:

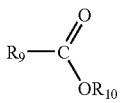

wherein $R_9$ is described above and $R_{10}$ is selected from the group consisting of hydrogen, and optionally-substituted linear or branched alkyl, alkene, cycloalkyl, cycloalkenyl, aryl, heteroatom-containing aryl, and aralkyl groups, to form an activated ester compound, and reacting the activated ester compound with an alcohol of structure:

$R_{11}$—OH thereby forming the monomeric ester compound.

In a further embodiment, the present invention provides compositions comprising the compounds prepared by the methods described above, wherein the composition further comprises a detectable amount of residual ester-substituted diaryl carbonate or the corresponding ester-substituted phenolic byproduct. In specific embodiments, the ester-substituted diaryl carbonate is BMSC.

BRIEF DESCRIPTION OF THE DRAWINGS

FIG. 11 shows a reaction scheme for the preparation of a monomeric ester in accordance with the invention.

DETAILED DESCRIPTION OF THE INVENTION

Figure 1:
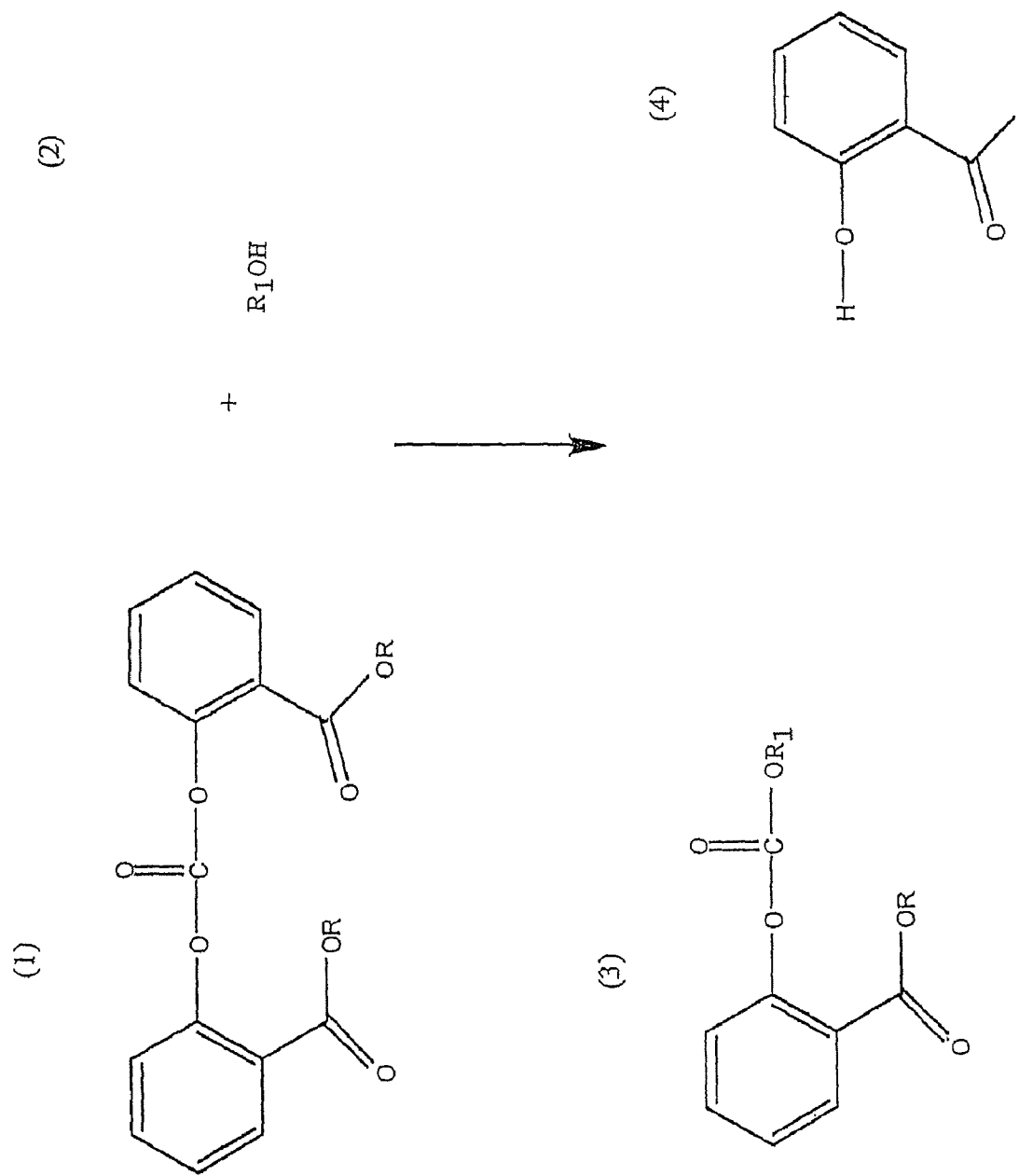
FIG. 1 shows a reaction scheme for the preparation of an intermediate monomeric carbonate in accordance with the invention.

The present invention provides a powerful synthetic method for the synthesis of monomeric carbonates and esters. The invention is of general applicability for reactions of primary, secondary, or tertiary alcohols (preferably primary or secondary in the case of cyclic monomeric carbonate preparations).

Definitions

As used in the specification and claims of this application, the following definitions, should be applied.

"a", "an", and "the" as an antecedent refer to either the singular or plural. For example, "an ester compound" refers to either a single species of compound or a mixture of such species unless the context indicates otherwise.

"Carbonate" refers to a class of chemical compounds sharing the same functional group "RO—C(O)—OR'" based on a carbonyl group flanked by an optionally substituted organic residues (e.g. R and R').

"Ester" refers to a class of chemical compounds sharing the same functional group "RO—C(O)—R'" based on an O—C(O) group flanked by an optionally substituted organic residues (e.g. R and R').

"Monomeric" carbonates and esters refers to compounds in which the carbonate or ester functional groups do not form a repeating unit in an oligomer or polymer chain. Where a reactant alcohol, acid, or ester is monofunctional, oligomerization and polymerization cannot occur. In the case where a reactant is difunctional (e.g. a diol, diacid, diester) such that oligomerization or polymerization could occur, this term refers to the portion of the product that is a non-oligomer and a non-polymer product, i.e. a cyclic product or a product with a free hydroxy group. The reactant alcohol, acid, and ester (e.g. mono- or di-functional reactants) are preferably selected the monomeric carbonates or esters have a molecular weight of no more than 3000 daltons, preferably no more than 2000 daltons, and most preferably no more than 1000 daltons.

"Asymmetric carbonates" refers to monomeric carbonate compounds having different or uneven substituents on either side of the —O—C(O)—O— carbonate linkage. Asymmetric monomeric carbonates may be cyclic or linear carbonates.

"Symmetric carbonate" refers to monomeric carbonate compounds having the same substituents or even substituents on either side of the —O—C(O)—O— carbonate linkage. Symmetric monomeric carbonates may be cyclic or linear carbonates.

"Cyclic carbonates" refers to monomeric carbonates wherein the —O—C(O)—O— carbonate linkage is a member of a ring. In the present invention, this ring is a 5 to 6 member ring wherein the —O—C(O)—O— carbonate linkage forms three members of the ring.

"Linear carbonates" refers to monomeric carbonates wherein the —O—C(O)—O— carbonate linkage is not member of a ring. The monomeric carbonate compound may contain optional substituents on either side of the —O—C(O)—O— carbonate linkage which may or may not be linear, branched, or contain a ring-type formation.

"Ester-substituted diaryl carbonates" refers to compounds of the general formula:

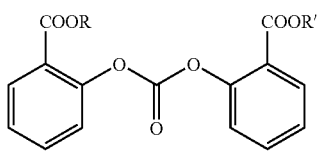

in which R and R' are individually alkyl, for example, methyl, ethyl, or propyl, aryl for example phenyl, or aralkyl, for example benzyl. A preferred ester-substituted carbonate is bismethyl salicyl carbonate (R=R'=methyl). (Ortho-alkoxycarbonylaryl)carbonates of this type are known for use in the preparation of polycarbonates, for example from U.S. Pat. Nos. 4,323,668; 6,420,512; 6,506,871; 6,548,623, 6,790,929, 6,518,391, and U.S. Patent Application Publications US 2003/0139529 and US 2003/0149223, all of which are incorporated herein by reference. Methods for making ester-substituted diaryl carbonates are described in US Patent Application Publication No. 2007/0282091 which is incorporated herein by reference.

"Optionally substituted" refers to the optional substituents for groups $R_1$ to $R_{11}$. The optional substituents for these groups may each independently be chemical functional groups that are not reactive under the transesterification conditions used to prepare the monomeric carbonate compounds. A non-limiting list of optional substituents include halogen, vinyl, carbonyl, ether, cycloether, azo, sulfide/thio, heterocyclic substituents, aldehyde, ketone, amide, nitro, nitrile, sulfoxide, sulfone, phosphates, phosphines, and phosphites.

Reference throughout the specification to "one embodiment," "another embodiment," "an embodiment," "some embodiments," and so forth, means that a particular element (e.g., feature, structure, property, and/or characteristic) described in connection with the embodiment is included in at least one embodiment described herein, and may or may not be present in other embodiments. In addition, it is to be understood that the described element(s) may be combined in any suitable manner in the various embodiments.

Numerical values in the specification and claims of this application reflect average values for a composition. Furthermore, unless indicated to the contrary, the numerical values should be understood to include numerical values which are the same when reduced to the same number of significant figures and numerical values which differ from the stated value by less than the experimental error of conventional measurement technique of the type described in the present application to determine the value.

Monomeric Carbonate Synthesis

Figure 2:
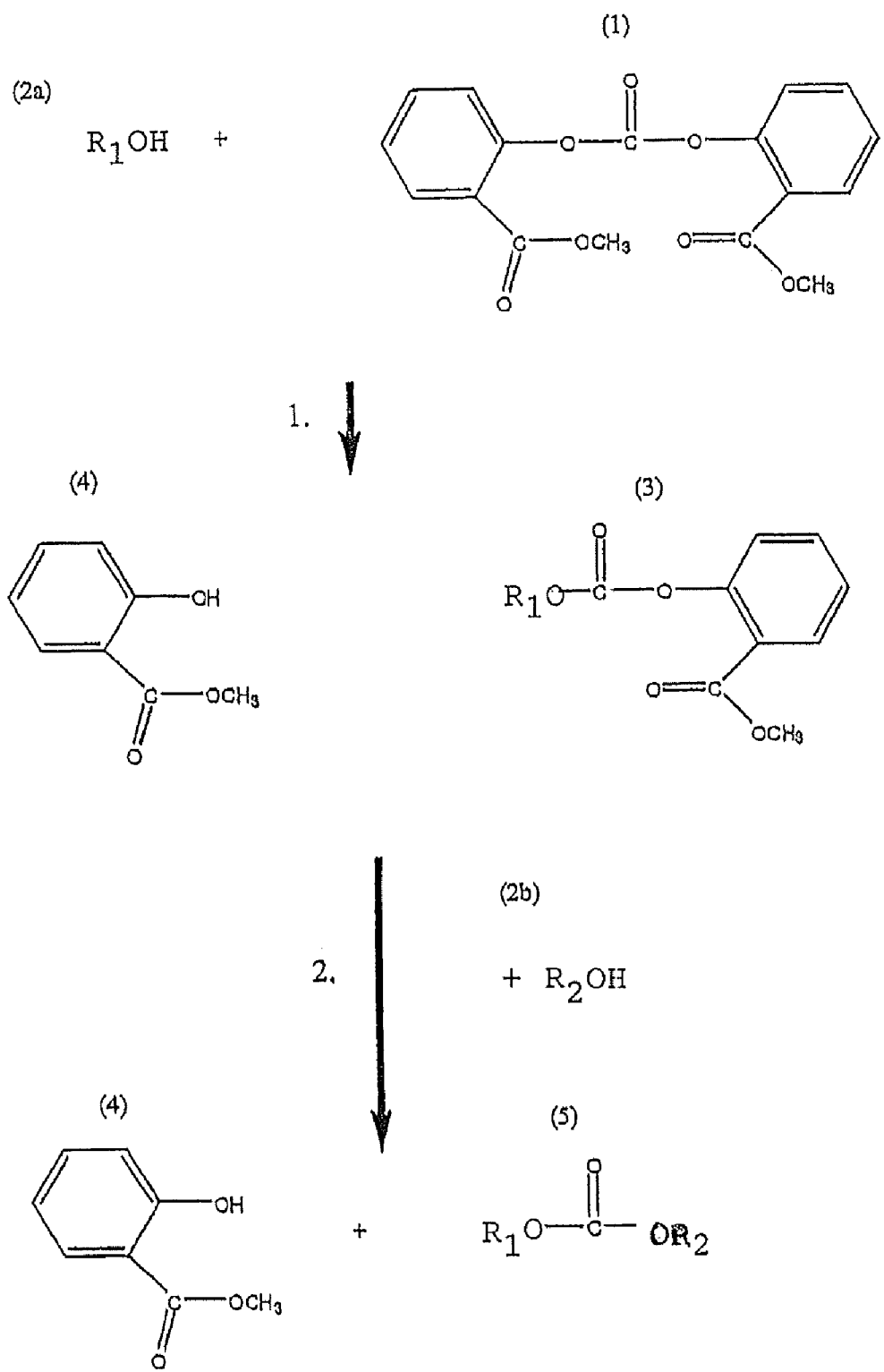
FIG. 2 shows a reaction scheme for the preparation of monomeric carbonates in accordance with the invention.

In one embodiment, a method for forming a monomeric carbonate comprises combining a monofunctional alcohol or a difunctional diol with an ester-substituted diaryl carbonate to form a reaction mixture, and allowing the reactions mixture to react to form a monomeric carbonate. The general preparation scheme for the synthesis of linear monomeric carbonates compound in accordance with the invention is shown in FIGS. 1 and 2. FIG. 1 shows a 1-step process to make an asymmetrical activated carbonate, and FIG. 2 shows a 2-step process to make an asymmetrical non-activated carbonate. It is also technically possible to make the asymmetrical non-activated carbonate $R_1OC(=O)OR_2$ by reacting 1 mole of BMSC directly with 1 mole of $R_1OH$ and 1 mole of $R_2OH$. A disadvantage of this 1-step process is that the desired asymmetrical carbonate, $R_1OC(=O)OR_2$, will potentially be contaminated with significant amounts of the symmetrical non-activated carbonates, $R_1OC(=O)OR_1$ and $R_2OC(=O)OR_2$.

As shown in FIGS. 1 and 2, an ester-substituted carbonate (1) is reacted together with a first optionally functionalized alcohol (2 in FIG. 1 and 2(a) in FIG. 2). The reaction yields an intermediate carbonate species (3) (e.g. an asymmetric activated carbonate species) and a phenolic byproduct (4). As shown in FIG. 2 the intermediate activated carbonate species (3) is then reacted with a second optionally functionalized alcohol (2(b)) to form more phenolic byproduct (4) and a linear monomeric carbonate compound (5) comprising units derived from the first and second alcohol.

The activating groups R of the ester-substituted diaryl carbonate are each independently an ortho-ester substituent. The ester substituent R may be alkyl, phenyl or benzyl (e.g. a methyl group in FIG. 2). The alcohol substituents $R_1$ and $R_2$ are each independently optionally-substituted linear or branched alkyl, phenyl, aryl or aralkyl groups. The optional substituents may each independently be chemical functional groups that are not reactive under the transesterification conditions used to prepare the monomeric carbonate compound (5). The phenolic byproduct (4) may be recycled to produce additional activated carbonate starting material, for example, by the phosgenation of the phenolic compound.

In this reaction, specific alcohol reactants and reactions conditions are selected in combination to arrive at the desired product. The reactions of alcohols with BMSC go essentially to full conversion even at relatively low reaction temperatures, e.g. room temperature. To make linear monomeric carbonates (e.g. from mono-functional alcohols) economically, it is preferred that the ester-substituted diaryl carbonate (e.g. BMSC) and the mono-functional alcohols (e.g. the first and second alcohol) are present in the theoretical-full-conversion molar ratio of 1:2. However, mole ratios (BMSC:alcohol) of equal to or between 0.80:2.2, for example 0.90:2.1 can be used. To make cyclic monomeric carbonates (e.g. from difunctional alcohols or diols), it is preferred that the ester-substituted diaryl carbonate (e.g. BMSC) and the diol are present in a molar ratio of 1:1. However, mole ratios (BMSC:alcohol) of equal to or between 0.90:1.1, for example 0.95:1.05 can be used.

In other embodiments a larger excess of either reactant may be employed. In one embodiment alcohol may be used in relation to the excess ester-substituted diaryl carbonate. This has the benefit of driving reaction toward full conversion. In one embodiment, where excess alcohol is used, a continuous or semi-continuous process may be employed where product monomeric carbonate is removed from the reaction components and the residual unreacted alcohol and ester-substituted diaryl carbonate is recycled or allowed to further react.

The reaction to form monomeric carbonate may be carried out in solution using inert solvents interfacially or in the melt. Suitable inert solvents include and are not limited to those where ester-substituted diaryl carbonate and the other reactants have sufficient solubility such as those in the following table:

| Solvent | Solubility at room temperature [g/L] |
|---|---|
| MeOH | <10 |
| EtOH | <10 |
| Et$_2$O | <10 |
| Hexane | 0 |
| THF | 159 |
| Ethyl Acetate | 61 |
| CH$_2$Cl$_2$ | 388 |
| CHCl$_3$ | 414 |
| DMSO | 109 |
| Toluene | 51 |
| DMF | 226 |
| Acetone | 118 |
| Acetonitrile | 124 |

BMSC is quite stable in these solvents, and no detectable MS formation is observed after >20 h storage time. Suitable reaction temperatures will typically be high enough to keep the solution or melt in the liquid form and not high enough to cause loss of the species 1, 2, 3, or 5 in FIGS. 1 and 2. The reaction temperature is less than 180° C., 160° C., 140° C. For example the reaction temperature may be less than 120° C., preferably less than 100° C., and sometimes more preferably less than 60° C. Higher reaction temperatures may be appropriate when more sterically hindered alcohols are used as reactants if longer reaction times are not acceptable.

In one embodiment, the reaction temperature may be selected such that product species 3 and 5 are devolatized to separate these reaction products from reactants and byproducts. In another the reaction temperature is selected such that byproduct 4 is devolatized to separate this reaction byproduct from the products. In a further embodiment, the reaction temperature is selected so that product species 3 and 5 and byproduct 4 are devolatized from the non-reacted reactants and later separated. Such a devolatization/reaction temperature schemes of the reaction products could be employed to help favor full conversion and make it easier to run the process continuously or semi-continuously (e.g. continuous feed of the reactants and devolatization of the reaction products). Adding a distillation column could also allow a proper separation of the components. However, it is important to note that more undesired side reactions and byproducts are observed at elevated reaction temperatures (e.g. at temperatures above about 150° C., especially above about 200° C.).

Water may optionally be present during the reaction, but it is important to limit the amount of water present because ester-substituted diaryl carbonates such as BMSC are readily hydrolyzed to methyl salicylate and even salicylic acid in the presence of basic compounds such as alcohols and water, especially at elevated temperatures, see for example, U.S. patent application Ser. No. 11/748,951, which is incorporated herein by reference. Therefore the amount of water present should be less than 1 mole %, preferably less than 100 ppm, more preferably less 10 ppm, and most preferably less than 1 ppm based on the concentration of the ortho-ester substituted diaryl carbonate. In one embodiment, water is essentially absent during the reaction of the ortho-ester substituted carbonate.

Reaction times may be 72 hours or less, preferably 24 hours or less, more preferably 12 hours or less, most preferably 4 hours or less. In some embodiments, the reaction time may be as little as 1 hour or less, preferably 30 minutes or less. Longer reaction times may be appropriate when more sterically hindered alcohols are used as reactants. The use of higher reaction temperatures typically enables shorter reaction times to be used, however more byproduct reactions (e.g. reactions involving the methyl ester group become more important in the melt, especially at elevated temperatures) are generally formed as higher reaction times are used.

Catalysts may optionally be used to increase the reaction rate, and suitable catalysts include transesterification catalysts, inorganic and organic bases, and metal oxide catalysts such as CaO, ZnO, MgO, ZrO$_2$, and Al$_2$O$_3$. In one embodiment, no catalyst is added. The use of optional catalysts may be preferable when more sterically hindered alcohols are used as reactants or when weaker-acid alcohols are used such as alkyl alcohols (e.g. versus stronger-acid phenolic alcohols) to maintain shorter reaction times and lower reaction temperatures. When catalyst is employed it is present in the reaction mixture in an amount of $1 \times 10^{-6}$ to 10 (e.g. 0.01 to 10 or 0.1 to 10) mole catalyst per mole of ester-substituted carbonate. The optimum catalyst level will be a function of the catalyst and reactant identities and the process conditions used. Typically less reactive reactants, less active catalysts, lower reaction temperatures, and shorter reaction times will require the use of higher catalyst concentrations.

Suitable alcohol reactants for use in the formation of linear monomeric carbonates are compounds of the formula HOR$_1$ and HOR$_2$, where R$_1$ and R$_2$ are independently optionally-substituted linear or branched alkyl (such as methyl, ethyl, n-propyl, iso-propyl, n-butyl and iso-butyl), alkene, cycloalkyl, cycloalkenyl, aryl, (for example phenyl, tolyl or xylyl), heteroatom-containing aryl, and aralkyl groups such as benzyl. A non-limiting list of suitable alcohol reactants includes: phenol, para-cumyl phenol, para-t-butylphenol, octylphenol, nonylphenol, and dodecylphenol.

The formation of symmetric linear monomeric carbonates can be achieved by using the same alcohol composition for both of alcohols R$_1$OH and R$_2$OH. The formation of asymmetric linear monomeric carbonates can be formed using a stepwise process in which an intermediate activated carbonate is formed by reacting a first alcohol with an ester-substituted diaryl carbonate in a molar ratio of approximately 1:1, and then the intermediate carbonate is further reacted with a second different alcohol also in a molar ratio of approximately 1:1. As described above, a excess molar ratio of the reactants may be employed. It is also technically possible to make the asymmetrical non-activated carbonate R$_1$OC(=O)OR$_2$ by reacting 1 mole of BMSC directly with 1 mole of R$_1$OH and 1 mole of R$_2$OH. A disadvantage of this later 1-step process is that the desired asymmetrical monomeric carbonate, R$_1$OC(=O)OR$_2$, will potentially be contaminated with significant amounts of the symmetrical non-activated carbonates, R$_1$OC(=O)OR$_1$ and R$_2$OC(=O)OR$_2$.

In another embodiment, the intermediate activated carbonate (e.g. the asymmetric activated carbonate having structure (3) in FIG. 1 or FIG. 2) can be isolated and used in separate processes (e.g. as an end capper for capping the free hydroxyl ends of polycarbonate to terminate or slow down polymerization reactions). In accordance with this embodiment the linear monomeric carbonate formation reaction proceeds without the use of R$_2$OH, or alternatively R$_2$OH could be considered to be the degradation product of the ester-substituted diaryl carbonate (e.g. methyl salicylate).

The present invention also provides a method of making cyclic monomeric carbonate compounds by reacting a diol with BMSC as well as a composition comprising the cyclic monomeric carbonate composition having residual ester-substituted diaryl carbonate or its degradation salicylate compound. The reaction conditions are suitably those as described above with regard to the preparation of linear monomeric carbonates. The cyclic monomeric carbonate has the structure:

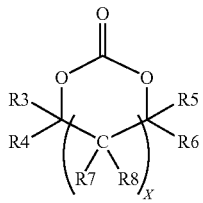

wherein X is 0 or 1, $R_3$, $R_4$, $R_5$, and $R_6$ are the same or different and are each independently selected from the group consisting of hydrogen, optionally-substituted linear or branched alkyl, alkene, cycloalkyl, cycloalkenyl, aryl, heteroatom-containing aryl, and aralkyl groups, or $R_3$ or $R_4$ in combination with $R_5$ or $R_6$ forms a ring structure (e.g. a five or six-member ring). When x=0, combinations of $R_3$ or $R_4$ and $R_5$ or $R_6$ may also be absent to form a double bond, and $R_7$ and $R_8$ when x is 1 are the same or different and are each independently selected from the group consisting of hydrogen, optionally-substituted linear or branched alkyl, alkene, cycloalkyl, cycloalkenyl, aryl, heteroatom-containing aryl, and aralkyl groups. Combinations of $R_7$ or $R_8$ with $R_3$, $R_4$, $R_5$, or $R_6$ may also be absent to form a double bond.

Reaction conditions that are believed to favor the formation of cyclic monomeric carbonates versus oligomers/polymers when diols are reacted with BMSC include: use of dilute solutions to minimize intermolecular reactions, use of low temperatures, and use of reduced reaction time inter alia. Also the use of diols that yield thermodynamically favored ring sizes such as 5 and 6 member rings is believed to enhance the cyclization, or the use of reactants such as pyrocatechol or 2-hydroxybenzyl alcohol in which the reactive alcohols are "fixed" in position on adjacent positions on an aromatic substrate thus in a favorable configuration for cyclization, as opposed to polymerization.

These cyclic monomeric carbonates are known as 1,3 dioxolanones or 1,3-dioxolan-2-ones, (e.g. 5 member rings comprising the 3 member —O—C(O)—O— group) and 1,3 dioxanones or 1,3-dioxan-2-ones, (e.g. 6 member rings comprising the 3 member —O—C(O)—O— group). The present method forms these compounds from the reaction of an ester-substituted carbonate with a diol compound having the general formula:

$HOR_3R_4C—(CR_7R_8)_X—CR_5R_6OH$

X, $R_3$, $R_4$, $R_5$, $R_6$, $R_7$, and $R_8$ are as described above. A non-limiting list of suitable diols for the preparation of cyclic monomeric carbonates include ethane diol, 1,2-propanediol, 1,3-propane diol, butanediol, 1,3-butanediol, 2,3-butanediol 2-methyl-1,3-propanediol, 1,2-cyclohexanediol, and catechol (1,2 dihydroxy benzene), among many other exemplary compounds.

Figure 3A:
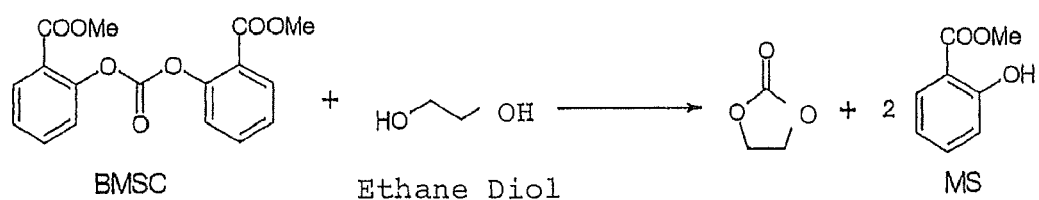
FIGS. 3(a) and 3(b) show reaction schemes for the preparation of cyclic monomeric carbonates in accordance with the invention.
Figure 3B:
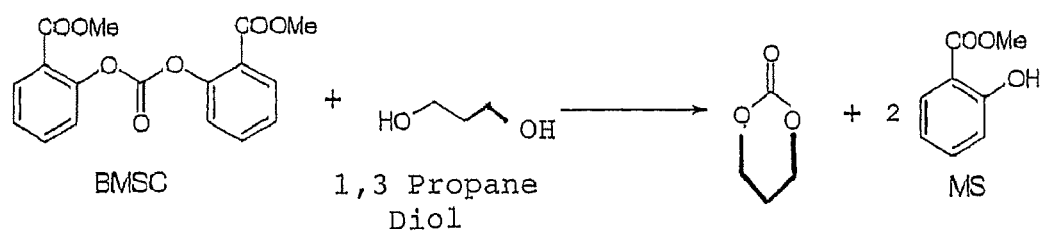

FIG. 3A shows the preparation of the cyclic monomeric carbonate compound 1,3 dioxolanone made by reacting ethane diol with BMSC. FIG. 3B shows the preparation of the cyclic monomeric carbonate compound 1,3 dioxanone (also known as "trimethylene carbonate") made by reacting 1,3 propane diol with BMSC.

Monomeric carbonates are useful compounds and are found in fuel additive preparations (e.g. See EP0474342 which is incorporated herein by reference), insecticide preparations, pharmaceutical and other medical preparations, and food preparations among many other useful preparations and compounds. A non-limiting list of linear monomeric carbonates of interest that can be prepared according to the methods of the present invention include: dimethylcarbonate, diethylcarbonate, methylethylcarbonate, methyl t-butyl carbonate, ethyl t-butyl carbonate, methyl t-amyl carbonate, ethyl t-amyl carbonate, di-t-butylphenyl carbonate, di-PCP carbonate, di-nonylphenyl carbonate, and those described in the following table:

| Monomeric carbonate | CAS # |
|---|---|
| 1-Chloroethyl, cyclohexyl carbonate | 99464-83-2 |
| 1-Chloroethyl, ethyl carbonate | 50893-36-3 |
| 1-Chloroethyl, isopropyl carbonate | 98298-66-9 |
| Dibutyl carbonate | 542-52-9 |
| Dioctyl carbonate | 1680-31-5 |
| Bis (2-ethylhexyl) carbonate | 14878-73-2 | among many other linear symmetric and asymmetric monomeric carbonate compositions. As described above, asymmetric activated monomeric carbonates (e.g. the intermediate carbonate of structure (3) in FIG. 2 or the final carbonate of structure (3) in FIG. 1) are also of capable of being produced by the methods of the present invention and include compounds such as methyl salicyl phenyl carbonate, methyl salicyl t-butylphenyl carbonate, and methyl salicyl nonylphenyl carbonate.

A non-limiting list of exemplary cyclic monomeric carbonate compounds include dioxolanones and dioxanones as described above and compounds disclosed in U.S. Pat. No. 4,344,881 which is incorporated herein by reference. The compounds are used in numerous preparations including bio-absorbable suture materials. See for example U.S. Pat. No. 4,705,820 and WO 1991/010004, which are incorporated herein by reference for all purposes. Other examples of cyclic monomeric carbonates include, but are not limited to, propylene carbonate, 1,2- and 2,3-butylene carbonate, phenylethylene carbonate 1,3-Benzodioxol-2-one (CAS # 2171-74-6), and 1,3-Dioxolan-2-one (CAS # 96-49-1), 1,3-Dioxan-2-one (CAS #2453-03-4), and 4H-1,3-Benzodioxin-2-one, and those found in the following table:

| Cyclic monomeric carbonate | CAS # |
|---|---|
| 1,3-dioxan-2-one | [31852-84-3] |
| 5,5-dimethyl-1,3-dioxan-2-one | [29035-08-3] |
| 5-ethyl-5-(hydroximethyl)-1,3-dioxan-2-one | [38802-97-0] |
| 5-[(allyloxi)methyl]-5-ethyl-1,3-dioxan-2-one | [3536-64-9] |
| 5,5_-[carbonyl bis-(oxymethylene)]-bis[5-ethyl-1,3-dioxan-2-one] | [84056-44-0] |
| 1,3,10,12-tetraoxo-cyclooctadecan-2,11-dione | [82613-63-6] |
| dibenzo [d,f]-[1,3] dioxepin-6-one | [7623-38-3] |
| 4,8-dicyclohexyl-2,10-dimethyl-12H-dibenzo [d,g] [1,3] dioxocin-6-one | [133126-34-8] |

Monomeric Ester Synthesis

Figure 11:
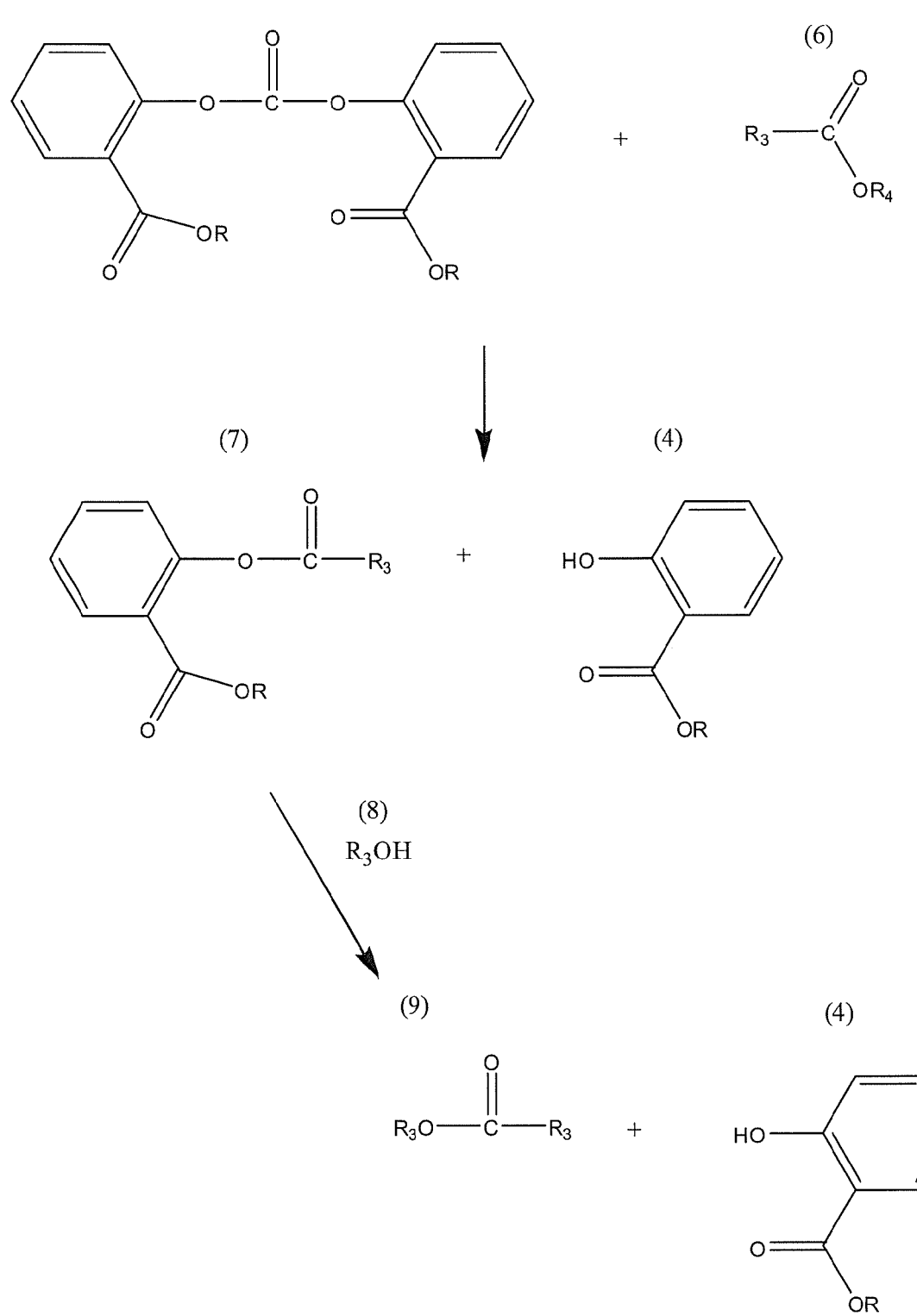

The general preparation scheme for the synthesis of activated ester compounds in accordance with the invention is shown in FIG. 11. An ester-substituted diaryl carbonate (1) (e.g. BMSC) is reacted with an ester or acid (6) to form the activated ester compound (7) and an ester-substituted phenol (4) (e.g. methyl salicylate). In another embodiment, the activated ester compound (7) may be further reacted with an alcohol (8) having the structure $R_3OH$ to form the monomeric ester compound (9) and more ester-substituted phenol (4). In a further embodiment, the ester-substituted diaryl carbonate, the acid or ester, and an alcohol are reacted together optionally in the presence of catalyst to form the monomeric ester compound.

The activated ester forming reaction and subsequent derivatization reaction can proceed under mild reaction conditions (e.g. low temperature and shorter reaction time), similar mole ratio conditions, and in the presence or absence of catalyst as described above with regard to the monomeric carbonate compound formation reactions. The activated ester forming reaction preferably will be done in the presence of a basic catalyst because the acidic functionality may act to quench reactivity. Also the temperature will preferably be high enough to bring about the decarboxylation reaction of the anhydride intermediate to form the final ester product, as shown in the second reaction step in the preparation of an activated ester in FIG. 10 (e.g. greater than 75° C., preferably greater than 100° C., and more preferably greater than 125° C.).

The present invention provides a method of forming an activated ester compound of the formula:

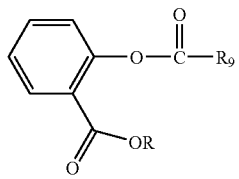

(7)

wherein R is an alkyl group, phenyl group, or a benzyl group, and $R_9$ is selected from the group consisting of optionally-substituted linear or branched alkyl, alkene, cycloalkyl, cycloalkenyl, aryl, heteroatom-containing aryl, and aralkyl groups. The method comprises reacting an ester-substituted diaryl carbonate as described above (e.g. BMSC) with a compound of the formula:

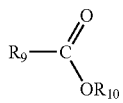

wherein $R_9$ is described above and $R_{10}$ is selected from the group consisting of hydrogen, and optionally-substituted linear or branched alkyl, alkene, cycloalkyl, cycloalkenyl, aryl, heteroatom-containing aryl, and aralkyl groups, thereby forming the compound. In a preferred embodiment $R_{10}$ is a lower molecular weight alkyl substituted (e.g. a $C_1$-$C_5$ branched or linear alkyl) or in a most preferred embodiment $R_{10}$ is hydrogen.

This activated ester compound may be further reacted with an alcohol of structure

$R_{11}$—OH wherein $R_{11}$ is selected from the group consisting of optionally-substituted linear or branched alkyl, alkene, cycloalkyl, cycloalkenyl, aryl, heteroatom-containing aryl, and aralkyl groups, to form a non-activated ester compound of the formula:

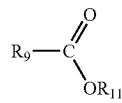

A non-limiting list of exemplary esters that are believed to be capable of being formed by the methods described herein include: Allyl hexanoate, Benzyl acetate, Bornyl acetate, Butyl butyrate, Ethyl acetate, Ethyl butyrate, Ethyl hexanoate, Ethyl cinnamate, Ethyl formate, Ethyl heptanoate, Ethyl isovalerate, Ethyl lactate, Ethyl nonanoate, Ethyl pentanoate, Geranyl acetate, Geranyl butyrate, Geranyl pentanoate, Isobutyl acetate, Isobutyl formate, Isoamyl acetate, Isopropyl acetate, Linalyl acetate, Linalyl butyrate, Linalyl formate, Methyl acetate, Methyl anthranilate, Methyl benzoate, Methyl benzyl acetate, Methyl butyrate (methyl butanoate), Methyl cinnamate, Methyl pentanoate (methyl valerate), Methyl phenylacetate, Nonyl caprylate, Octyl acetate, Octyl butyrate, Amyl acetate (pentyl acetate), Pentyl butyrate (amyl butyrate), pentyl hexanoate (amyl caproate), Pentyl pentanoate (amyl valerate), Propyl ethanoate, Propyl isobutyrate, Terpenyl butyrate and those found in the following table:

| Some Commercially Important Esters |
| --- |
| di(2-ethylhexyl) phthalate |
| 2-ethylhexyl 4-methoxycinnamate |
| methyl cinnamate |
| methyl 4-hydroxybenzoate |
| di(2-ethylhexyl) adipate |
| Geocillin, CAS # [35531-88-5] |
| 2,2,4-trimethyl-1,3-pentanediol monoisobutyrate |

The present invention also provides a method of forming a cyclic monomeric ester compound. When the carboxylic acid and hydroxy groups are present in the same molecule, a lactone (e.g. a monomeric cyclic ester) may form. Lactonization occurs with gamma- and delta-hydroxy acids that form unstrained five- and six-membered rings. In the present embodiment an ester-substituted diaryl carbonate (e.g. BMSC) is reacted with a compound having both a carboxylic acid/ester group and an alcohol group to make a cyclic ester product. For example, β-propiolactone, is formed by a reaction of BMSC together with β-hydroxypropionic acid.

Cyclic monomeric esters have significant commercial importance. A non-limiting list of commercially important lactones that can be produced by the method described above include diketene and β-propanolactone (used in the synthesis of acetoacetic acid derivatives) and β-substituted propanoic (propionic) acids, respectively; the perfume ingredients pentadecanolide and ambrettolide; vitamin C; and the antibiotics methymycin, erythromycin, and carbomycin. Other cyclic monomeric esters that can be produced by the method of the present embodiment include: β-propiolactone, γ-butyrolactone (GBL), D-glucono-δ-lactone (E575: a food additive), and ?-caprolactone.

EXAMPLES

Having described the invention in detail, the following examples are provided. The examples should not be considered as limiting the scope of the invention, but merely as illustrative and representative thereof.

(WE) as used herein is understood to mean "working example" while (CE) is understood to mean "comparative example". The terms "working" and "comparative" are simply used to demonstrate comparisons to other examples. Working and comparative examples may or may not be an example within the scope of the present invention.

In the following examples the following processes, measurements, and experimental tests were performed.

I: Symmetric and Asymmetric Linear Monomeric Carbonate Synthesis with Bismethylsalicylcarbonate (BMSC)

Example 1

Synthesis of Di-PCP Carbonate from BMSC and Para-Cumylphenol (PCP)

Figure 4A:
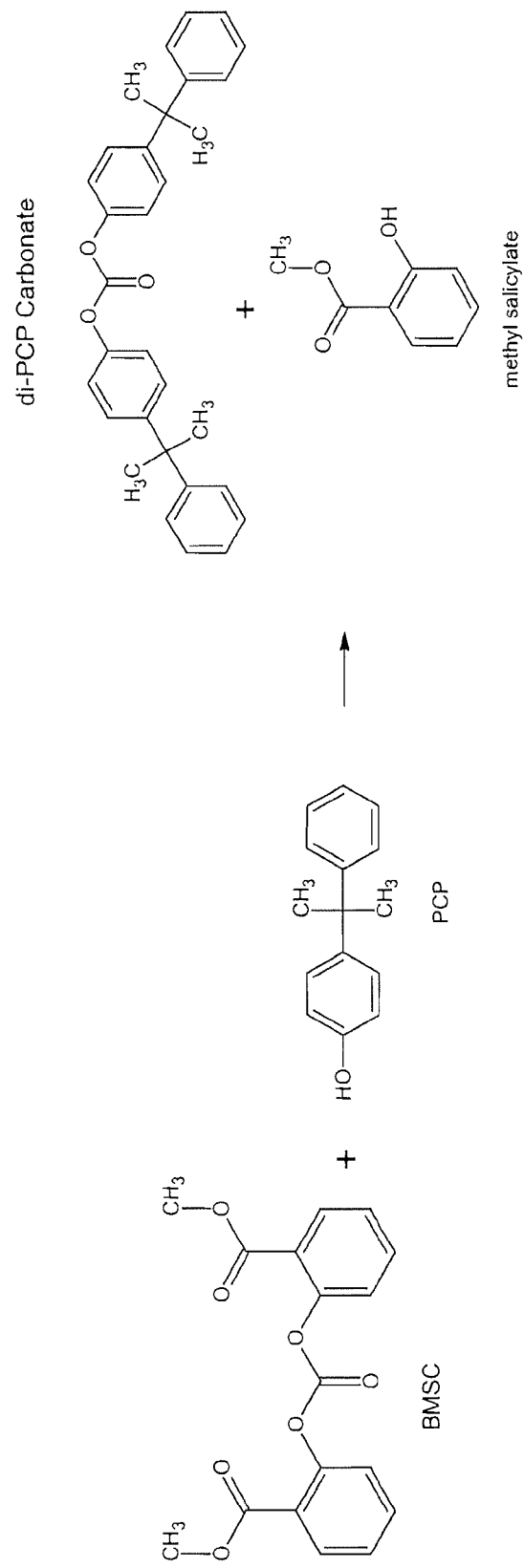
FIGS. 4(a), 5(a), 6, 7, 8, 9, 10, 11, 12 (Comparative Ex.), 13 (Comparative Ex.), and 14 show reaction schemes for the preparation of monomeric carbonates and esters in accordance with the example section.

The reaction scheme and mechanism for this reaction is depicted in FIG. 4(a).

The synthesis was carried out in 100 mL round bottom flasks that had been treated in a HCl solution (1M) for 24 hours in order to remove all traces of sodium ions that could be present on the glass surface and act as a catalyst in the reaction. The synthesis was carried out at a 1/2 BMSC/PCP molar ratio. 1 mol % of NaOH relative to BMSC was used as a catalyst.

First 6 grams of BMSC were weighed in a 25 ml screw neck vial, and then 13 ml of chloroform was added to the vial and shaken for 20 minutes. 7.71 grams of PCP were dissolved in 6 mLs of chloroform in a round bottom flask while stirring. Once the PCP was dissolved, 3.4 µL of catalysts (NaOH) were added. The BMSC solution was then added drop-wise to the round bottom flask. The reaction was performed at room temperature (RT) for 4 hours.

Figure 4B:
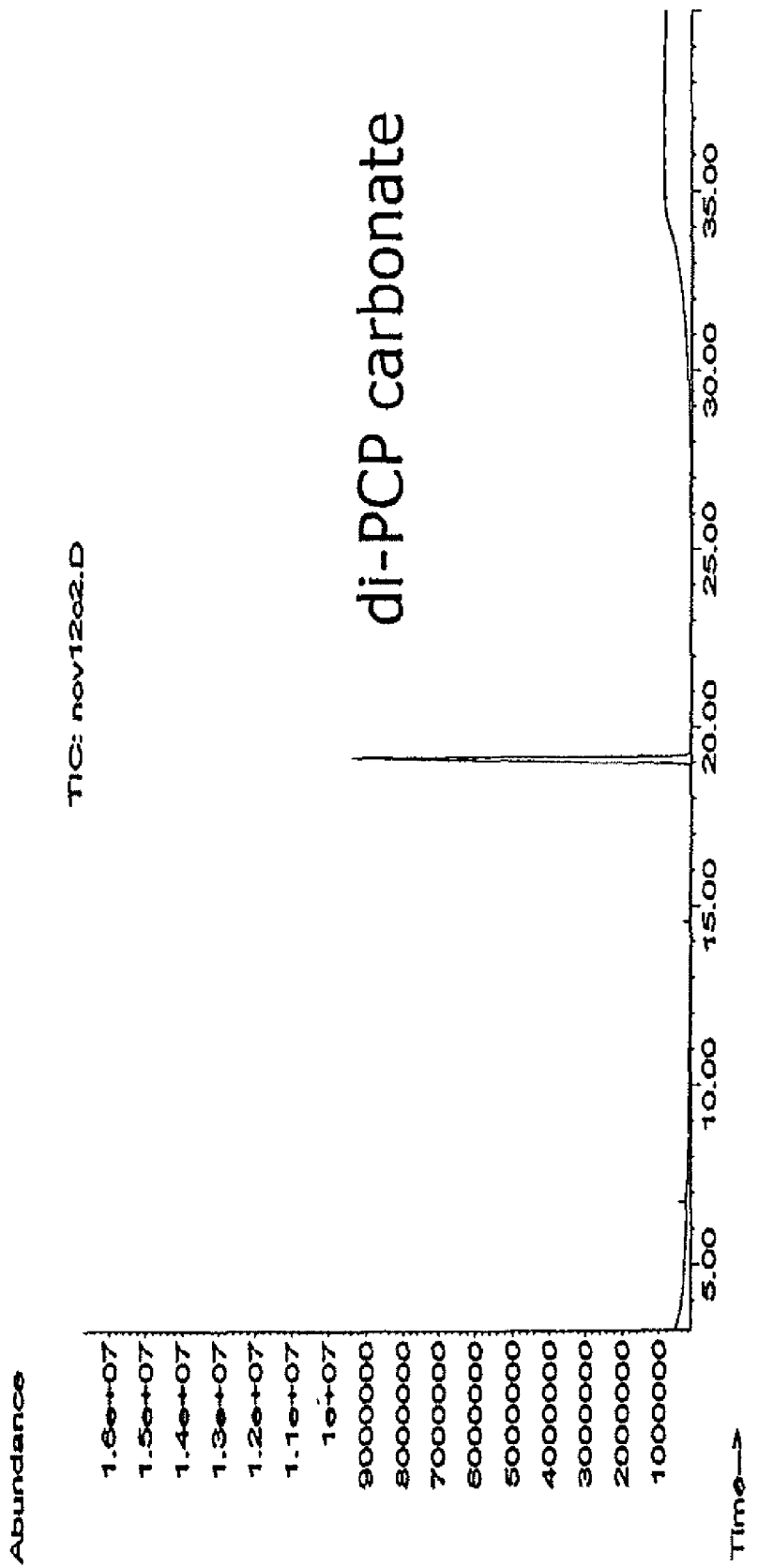
FIGS. 4(b), 4(c), 5(b), 5(c), show graphical results from the Example section.
Figure 4C:
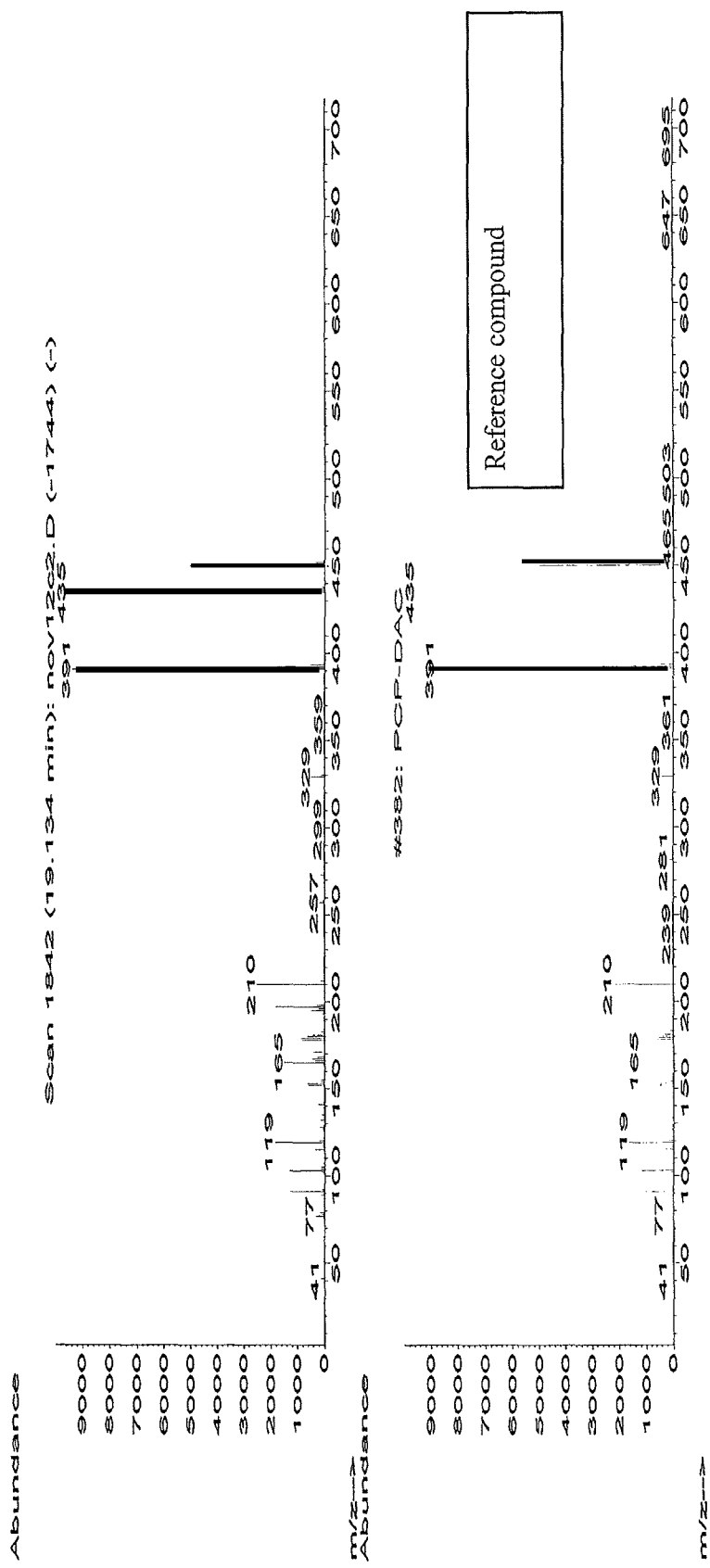

Analytical results for Example 1 (di-PCP Carbonate synthesis) are as follows. Analysis was made using high temperature GC-MS (Gas Chromatography Mass Spectrometer), peaks were identified by comparison to a measurement carried out on a reference compound. Samples were dissolved in dichloromethane at concentrations of approx 500-1000 ppm. FIG. 4(b) shows that the di-PCP Carbonate was obtained in high yield and in quite pure form. FIG. 4(c) confirms the identity of the synthesized di-PCP Carbonate by comparison with the mass spectral data for a reference di-PCP sample.

Example 2

Synthesis of Monocapped PCP Carbonate (PCP Methyl Salicyl Carbonate)

Figure 5A:
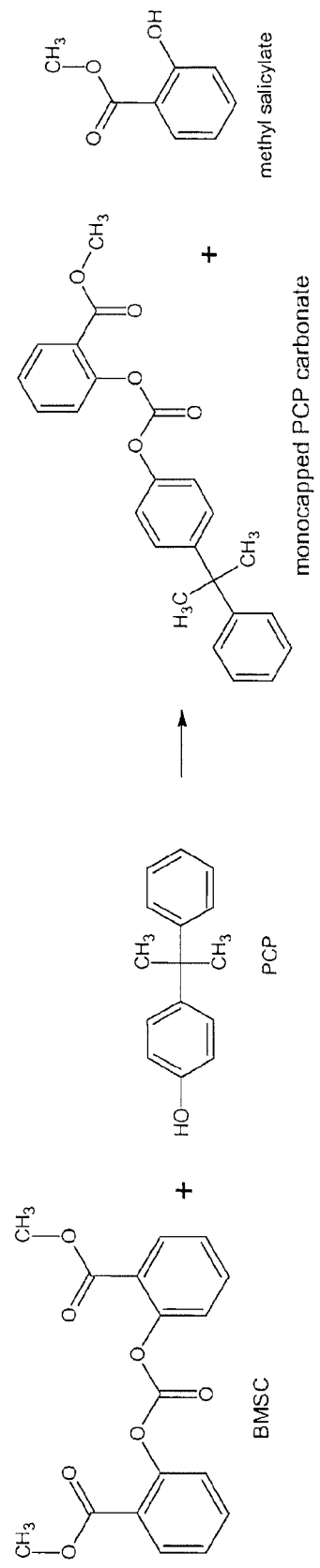

The reaction scheme and mechanism for this reaction is depicted in FIG. 5(a).

The procedure for example 1 was repeated, except a molar ratio of 1/1 BMSC/PCP was used.

Figure 5B:
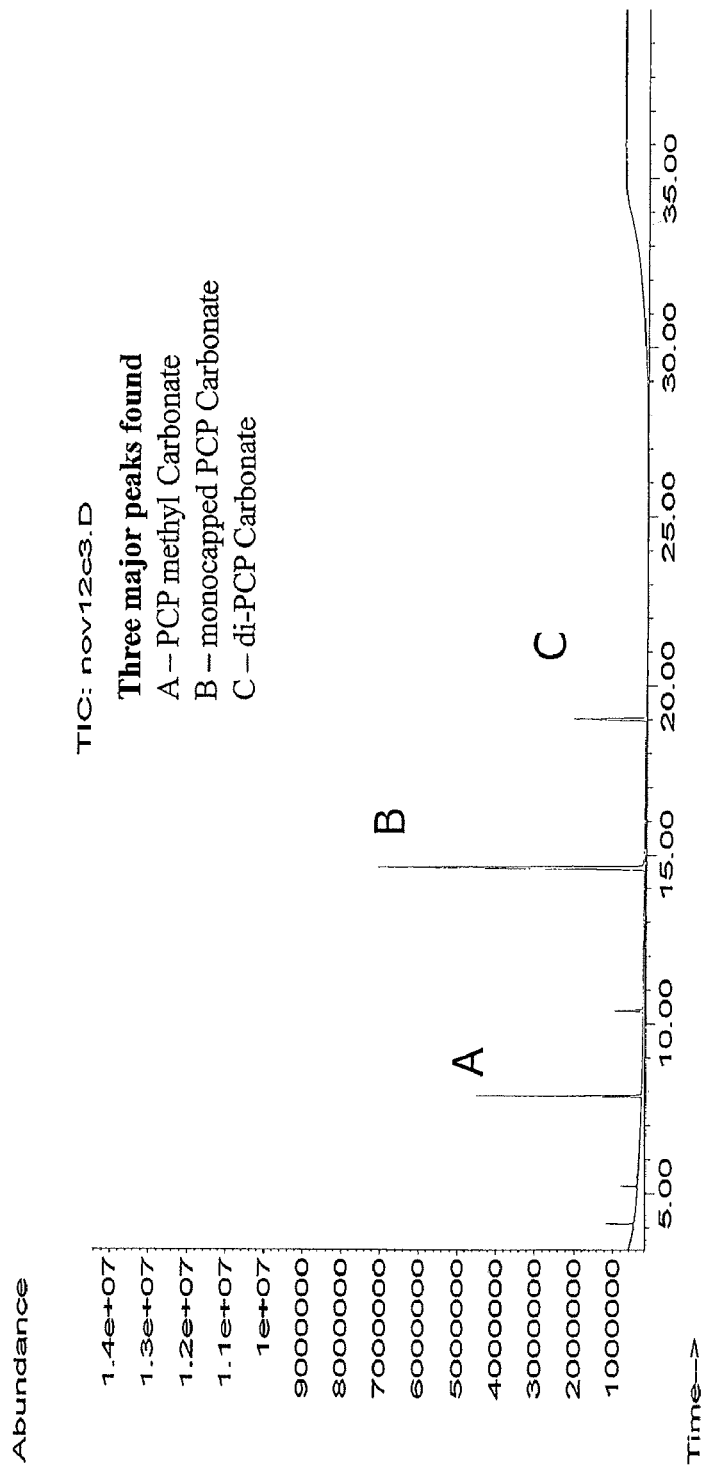
Figure 5:
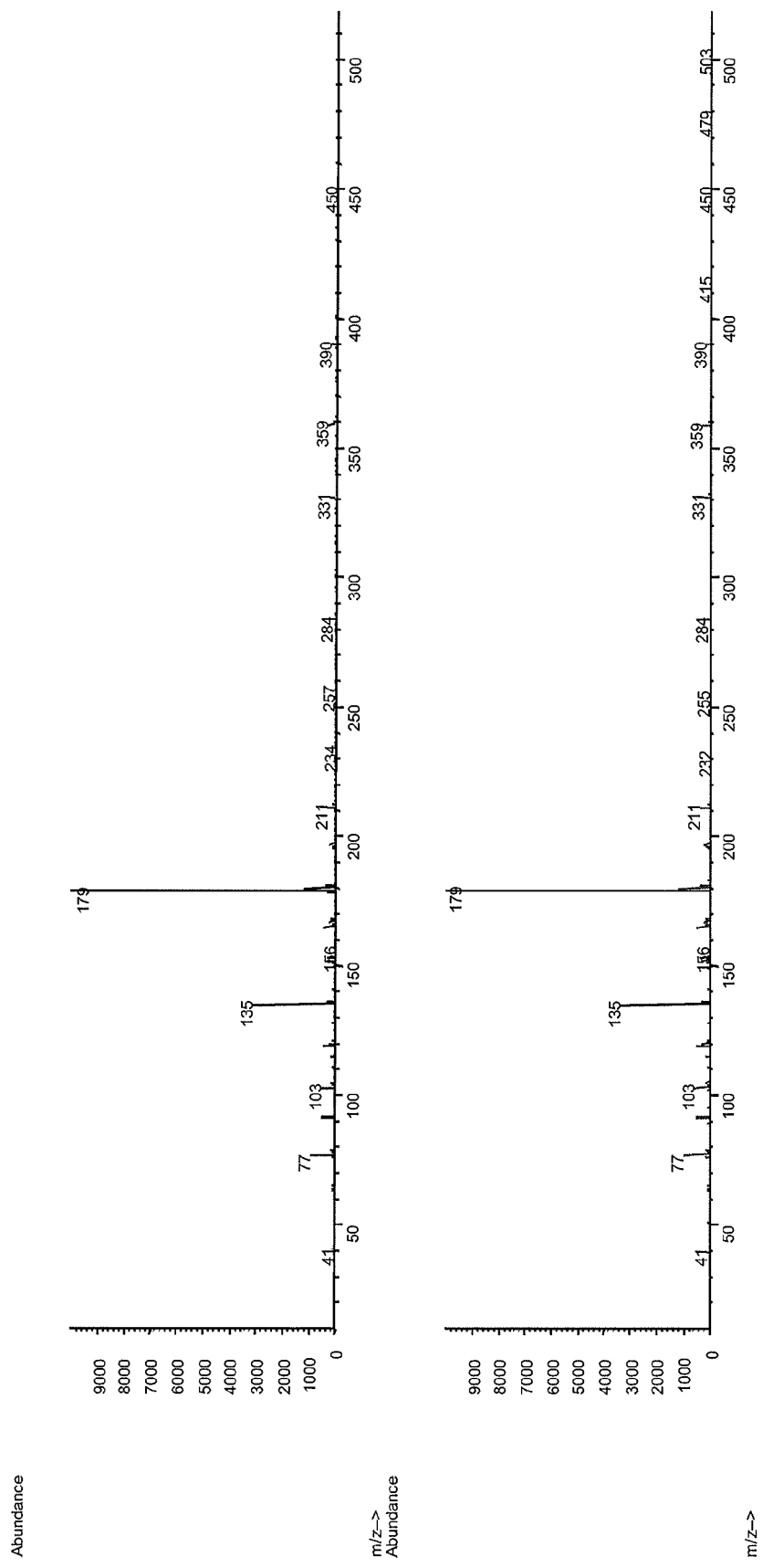

Analytical results for Example 2 (PCP methyl salicyl carbonate) are as follows. GC-MS analysis was carried out as for Example 1, and a comparison was made with the mass spectral data for a reference PCP methyl salicyl carbonate compound. The results indicate that the dominant reaction product was the monocapped PCP carbonate (PCP methyl salicyl carbonate). See FIGS. 5(b) and 5(c).

Example 3 (Comparative)

Figure 12:
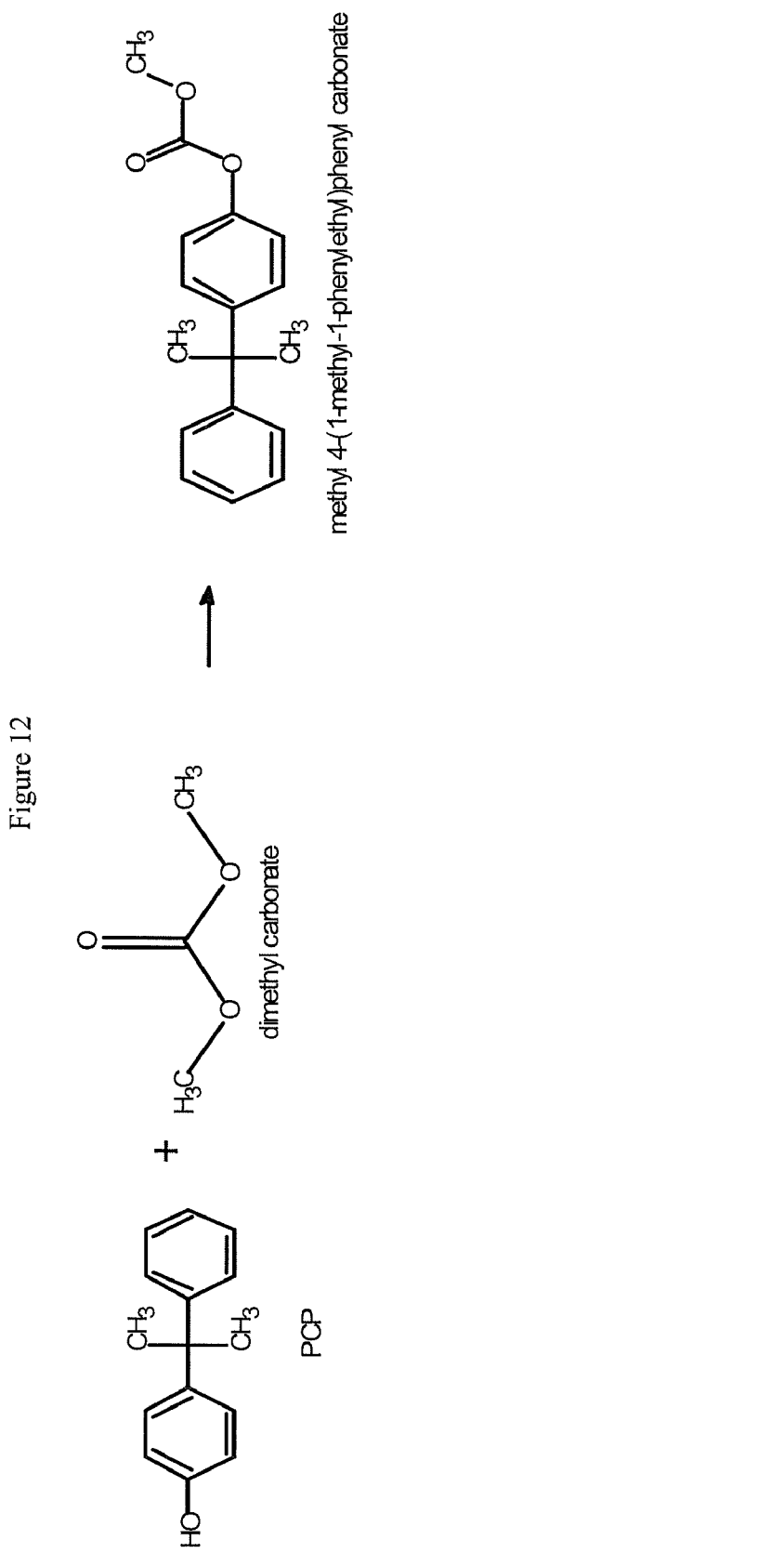

Synthesis of Asymmetric Monomeric Carbonate from PCP Using Dimethyl Carbonate (DMC) Instead of BMSC The reaction scheme and mechanism for this reaction is depicted in FIG. 12.

The synthesis was carried out using same procedure as in Example 2, except that a 1:1 PCP:DMC molar ratio was used.

3.855 grams of PCP and 0.63 ml DMC were added to the flask instead of BMSC.

The reaction product was analyzed by HPLC using the method of Example 2, and the chromatogram indicated that no conversion had occurred in this reaction of PCP and DMC.

Example 4 (Comparative)

Figure 13:
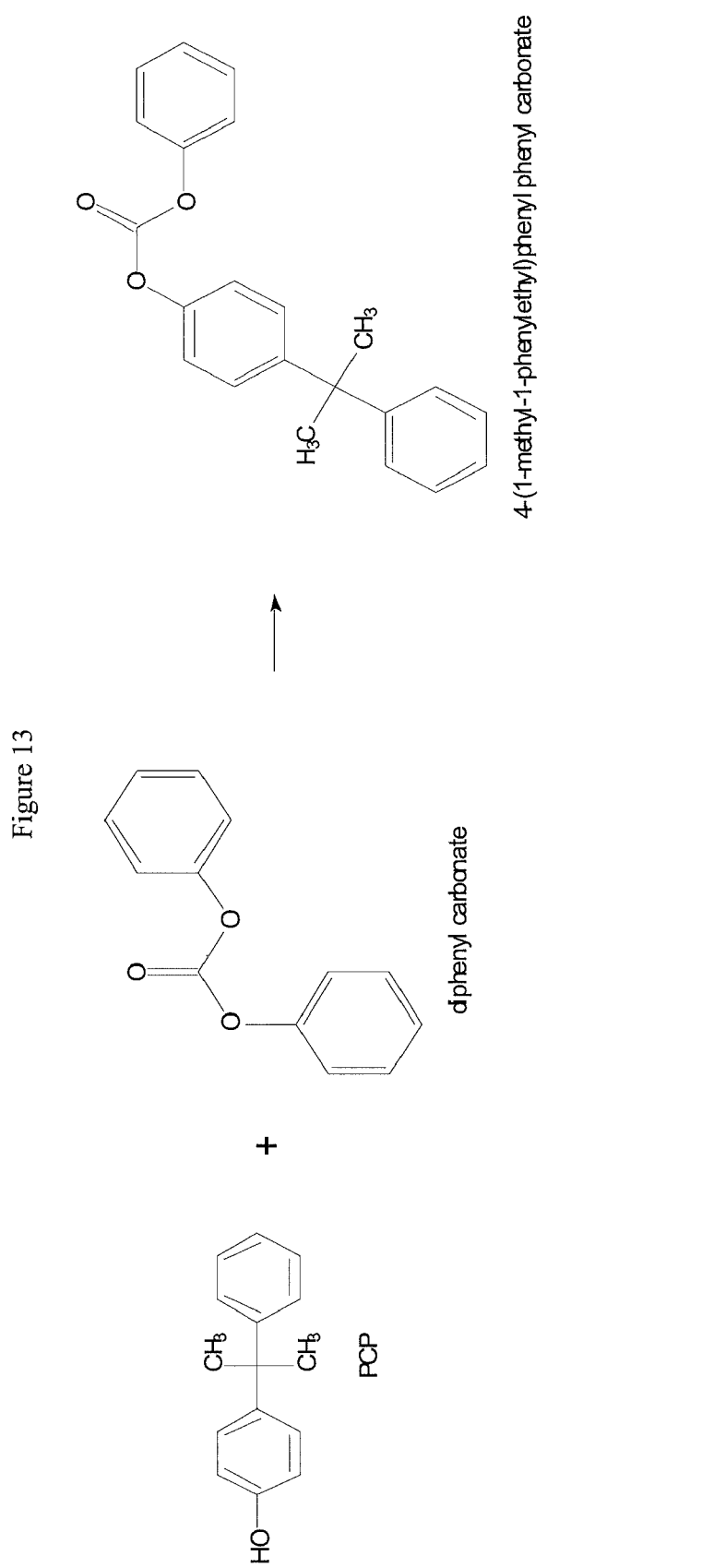

Synthesis of Asymmetric Monomeric Carbonate from PCP Using Diphenyl Carbonate (DPC) Instead of BMSC The reaction scheme and mechanism for this reaction is depicted in FIG. 13.

The synthesis was carried out under the same reaction conditions and setup described in Example 2, except that a 1:1 PCP:DPC molar ratio was used. 3.89 grams of DPC were added to the flask, instead of DMC.

The reaction product was analyzed by HPLC and GC-MS using the method of Example 2, and the chromatograms indicated that only trace level conversion had occurred in this reaction of PCP and DPC.

Example 6

Synthesis of Asymmetric Monomeric Carbonate from BMSC and o-Cresol

The reaction scheme and mechanism for this reaction is depicted in FIG. 14.

The synthesis was carried out under the same reaction conditions and setup as described in Example 2 except that 1.92 mL of o-cresol was reacted with BMSC. The reaction was performed at 61° C. for 4 hours.

The reaction product was analyzed by HPLC and GC-MS using the method of Example 2, and the chromatograms indicated that only partial conversion had occurred in this reaction of o-cresol and BMSC.

Example 7

Synthesis of PCP Methyl Salicyl Carbonate from the Melt of BMSC and PCP

The reaction scheme and mechanism for this reaction is depicted in FIG. 5(a).

The synthesis was carried out using the same procedure as in Example 1 except that 6 grams of BMSC and 3.85 grams of PCP were weighed in a 100 ml round bottom flask. Then 3.4 L of catalysts (NaOH) were added using a micro syringe. The reaction was heated to 180° C., and left for 2 hours.

The formation of the monocapped PCP carbonate product (PCP methyl salicyl carbonate) as the major product was confirmed using the same method as described for high temperature GC/MS as in Example 1.

II: Cyclic Monomeric Carbonate Synthesis with Bismethylsalicylcarbonate (BMSC)

Example 8

Synthesis of 1,3-dioxolan-2-one

Figure 6:
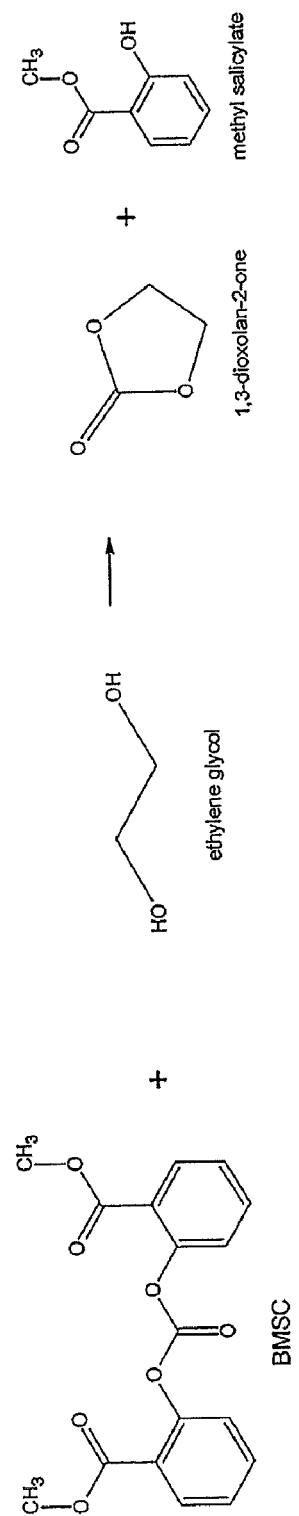

The reaction scheme and mechanism for this reaction is depicted in FIG. 6.

The reaction was carried out in a 3 neck round bottom flask, which was treated for 24 hours in a 1M HCL bath to remove sodium traces. The synthesis was performed at a 1/1 molar ratio of BMSC/ethylene glycol. 0.5 mol % of NaOH (1M) was used as a catalyst for the reaction. 1.982 grams of BMSC were dissolved in a round bottom flask with 10 mL of chloroform and mixed with 0.33 mL of ethylene glycol, followed by 0.19 ml of NaOH while stirring. The synthesis was carried out under nitrogen at 61° C. for 90 min in the round bottom flask which was equipped with a distillation column to provide reflux and to ensure that the BMSC remained in the reaction media. The formation of the 1,3-dioxolan-2-one was confirmed by a combination of GCFID and GC-MS and/or LC-MS methods.

Example 9

Synthesis of 1,3-benzodioxol-2-one

Figure 7:
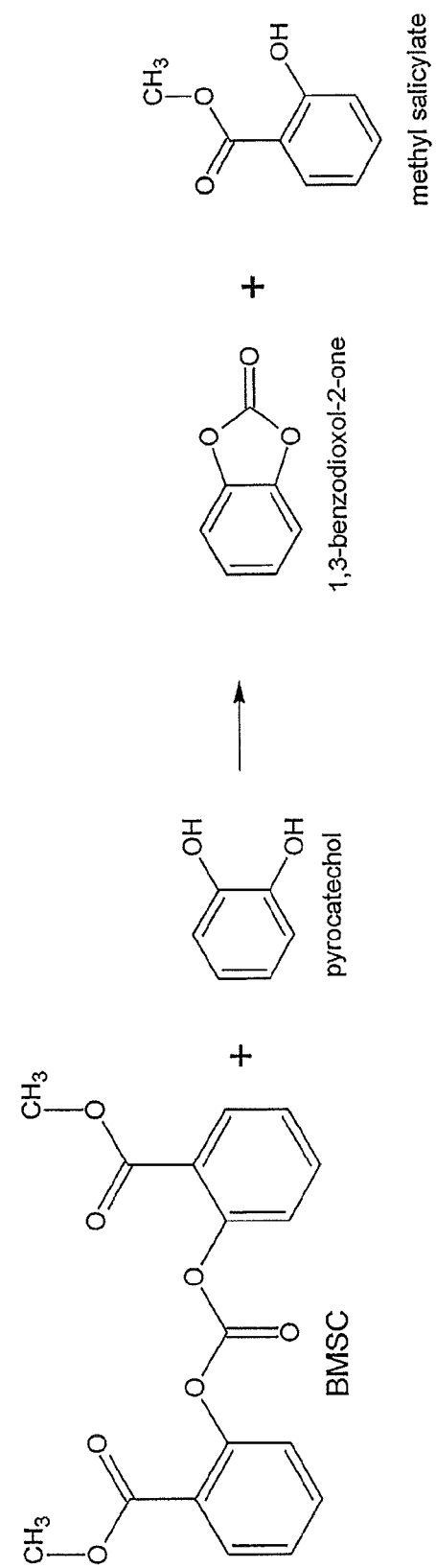

The reaction scheme and mechanism for this reaction is depicted in FIG. 7.

The synthesis is carried out under the same reaction conditions and setup described in Example 8, except that 1.982 grams of BMSC are dissolved in 10 mL of chloroform, 0.66 grams of pyrocatechol are added, followed by 0.25 mL of triethylamine to a round bottom flask while stirring. The formation of the 1,3-benzodioxol-2-one was confirmed by a combination of GCFID and GC-MS and/or LC-MS methods.

Example 10

Synthesis of 1,3-dioxan-2-one

Figure 8:
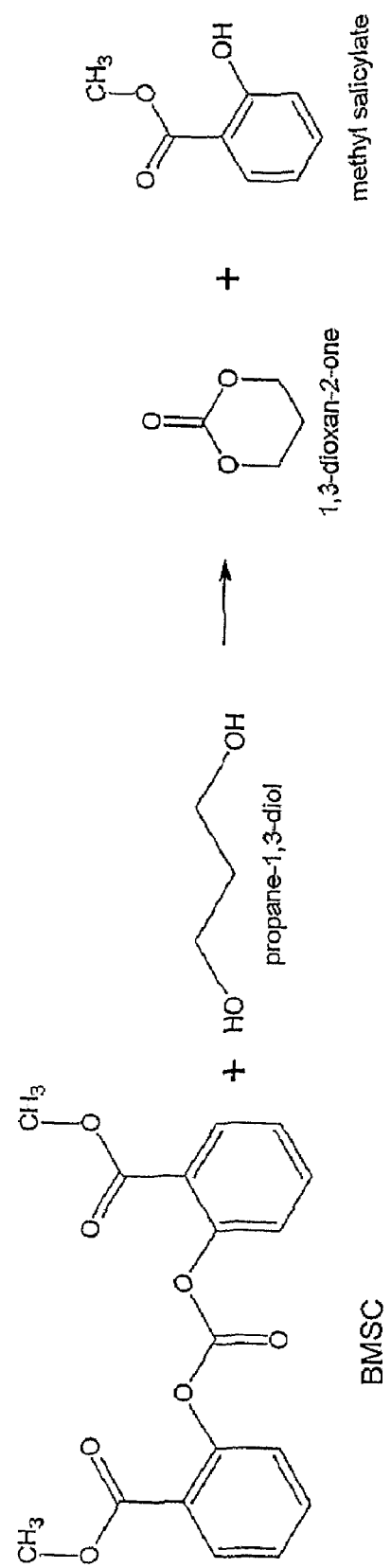

The reaction scheme and mechanism for this reaction is depicted in FIG. 8.

The synthesis was carried out under the same reaction conditions and setup as described in Example 8 except that 1.982 grams of BMSC were dissolved with 10 mL of chloroform in a round bottom flask. Then 0.434 mL of propane-1, 3-diol was added, followed by 0.19 mL of NaOH while stirring. The formation of the 1,3-dioxan-2-one was confirmed by a combination of GCFID and GC-MS and/or LC-MS methods.

Example 11

Synthesis of 4H-1,3-benzodioxin-2-one

Figure 9:
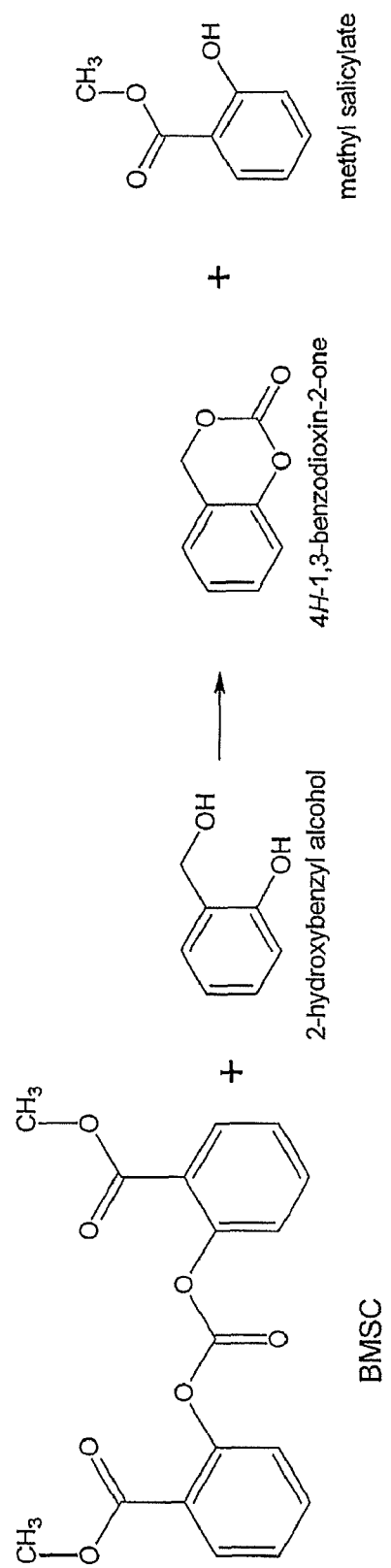

The reaction scheme and mechanism for this reaction is depicted in FIG. 9.

The synthesis was carried out under the same reaction conditions and setup as described in Example 8 except that, 1.982 grams of BMSC were dissolved with 10 mL of chloroform in a round bottom flask while stirring. Then 0.745 grams of 2-hydroxybenzyl alcohol was added, followed by 0.19 mL of NaOH (0.5 mol %). The formation of the 4H-1,3-benzodioxin-2-one was confirmed by a combination of GCFID and GC-MS and/or LC-MS methods.

III: Monomeric Ester Synthesis with Bismethylsalicylcarbonate (BMSC)

Figure 10:
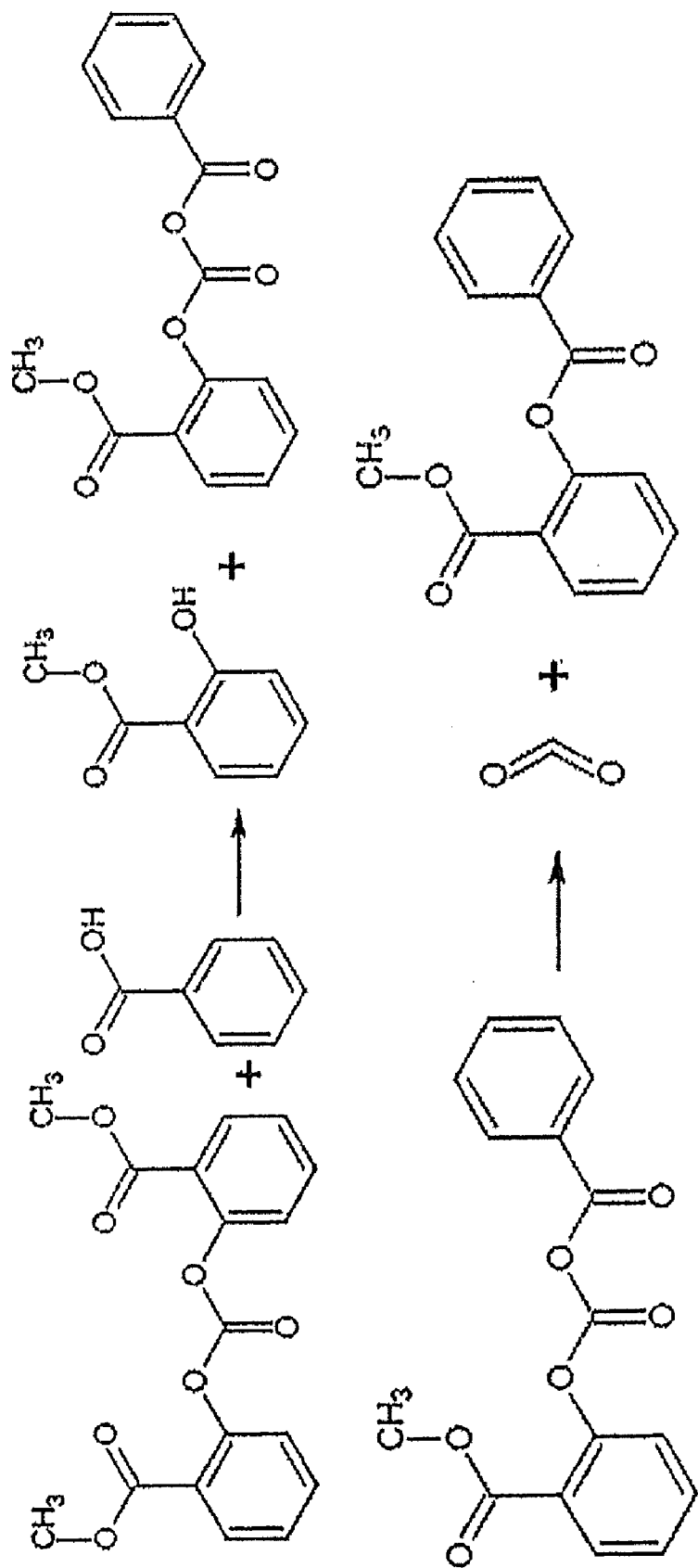

The reaction scheme and mechanism for the reaction of examples 12-21 is depicted in FIG. 10. The following ester syntheses reaction examples (e.g. methyl benzoylsalicylate (ester) formation) are based on the reaction of BMSC with the following carboxylic acid (benzoic acid):

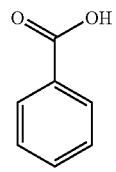

Example 12

The synthesis was carried out in reaction tubes that had been treated in an HCl (1M) solution for 24 hours in order to remove all traces of sodium ions that could be present on the glass surface and act as a catalyst in the reaction. The reaction was carried out by melting 1 g BMSC, 0.3697 g of benzoic acid in the presence of a catalyst (0.012 g of NaOH) at a temperature of 150° C. Subsequently, the reaction mixture was stirred for 15 minutes at 150° C.

During stirring a white solid was formed and TDS-GC-MS analysis showed that methyl benzoylsalicylate (ester) has been formed.

Example 13

The synthesis was carried out in 100 mL round bottom flasks that had been treated in an HCl solution (1M) for 24 hours in order to remove all traces of sodium ions that could be present on the glass surface and act as a catalyst in the reaction. The reaction was carried out by dissolving 6 g of BMSC and 2.22 g of benzoic acid in 20 ml of chloroform. Subsequently, the reaction mixture was stirred during 30 minutes at room temperature.

TDS-GC-MS analysis confirmed that the sample contains traces of the methyl benzoylsalicylate (ester). The sample mostly consisted out of unreacted BMSC, unreacted benzoic acid, and methylsalicylate.

Example 14

The procedure of example 13 was repeated except that a catalyst was added. As a catalyst 0.088 g of NaOH is added, this corresponds to a 10 mole % based on the benzoic acid.

TDS-GC-MS analysis confirmed that the sample contains traces of the methyl benzoylsalicylate (ester). The sample mostly contains out of unreacted BMSC, unreacted benzoic acid, and methylsalicylate.

Example 15

The synthesis was carried out in reaction tubes that had been treated in an HCl solution (1M) for 24 hours in order to remove all traces of sodium ions that could be present on the glass surface and act as a catalyst in the reaction. The reaction was carried out by dissolving 1 g of BMSC and 0.3697 g of benzoic acid in 6 ml of chloroform. Subsequently, the reaction mixture was stirred during 30 minutes at 61° C. (reflux).

TDS-GC-MS analysis confirmed that the sample contains traces of the methyl benzoylsalicylate (ester). The sample mostly consisted out of unreacted BMSC, unreacted benzoic acid, and methylsalicylate.

Example 16

The procedure of Example 15 was repeated except that a catalyst was added. As a catalyst 0.012 g NaOH is added, this corresponds to a 10 mole % based on the benzoic acid.

During the reaction a white precipitate was formed in the reaction mixture. After the reaction was stopped the white substance was filtrated out of the mixture. The solution was analyzed by TDS-GC-MS and showed to contain traces of the ester but the mixture mostly consisted out of unreacted BMSC, unreacted benzoic acid, and methylsalicylate. The TDS-GC-MS analysis results show that the precipitate consisted of unreacted BMSC, unreacted benzoic acid, and methylsalicylate.

Example 17

The procedure of Example 13 was repeated except that the solvent has changed to toluene and the reaction was carried out at reflux conditions (111° C.).

TDS-GC-MS analysis confirmed that the sample contains traces of the methyl benzoylsalicylate (ester). The sample mostly contains out of unreacted BMSC, unreacted benzoic acid, and methylsalicylate.

Example 18

The procedure of Example 17 was repeated except that a catalyst was added. As a catalyst 0.012 g NaOH is added, this corresponds to a 10 mole % based on the benzoic acid.

During the reaction a white precipitate was formed in the reaction mixture. After the reaction was stopped the white substance was filtrated out of the mixture. The solution was analyzed by TDS-GC-MS and showed to contain traces of the ester but the mixture mostly consisted out of unreacted BMSC, unreacted benzoic acid, and methylsalicylate. The TDS-GC-MS analysis results show that the precipitate consisted of unreacted BMSC, unreacted benzoic acid, and methylsalicylate.

Example 19 (Comparative)

The procedure of example 16 was repeated except that 1 g DPC and 0.5700 g of benzoic acid, which corresponds to a 1:1 molar ratio, in the presence of a catalyst (0.018 g NaOH) were solved in 6 ml chloroform.

TDS-GC-MS results show that no ester was formed.

Example 20 (Comparative)

The procedure of example 16 was repeated except that 0.25 g DMC and 1.3558 g of benzoic acid, which corresponds to a 1:1 molar ratio, in the presence of a catalyst (0.044 g NaOH) were solved in 6 ml chloroform.

TDS-GC-MS results show that no ester was formed.
The syntheses reactions of Examples 21 and 22 are based on the reaction of BMSC (Ex. 21) or DPC (Ex. 22) with the following carboxylic acid (propionic acid):

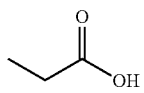

Example 21

The synthesis was carried out in reaction tubes that had been treated in an HCl (1M) solution for 24 hours in order to remove all traces of sodium ions that could be present on the glass surface and acts as a catalyst in the reaction. The reaction was carried out by melting 1 g of BMSC, 0.2242 g of propionic acid, which corresponds with a molar ratio of 1:1 (BMSC:propionic acid), in the presence of a catalyst (0.012 g of NaOH) at a temperature of 125° C. Subsequently, the reaction mixture was stirred for 15 min at 125° C.

The sample was analyzed by HPLC. The yield, calculated based on the total peak area, is 34%. TDS-GC-MS confirmed the structure of the ester.

Example 22 (Comparative)

The procedure of example 21 was repeated except 1 g of DPC, 0.3458 g of propionic acid, was melted in the presence of a catalyst (0.018 g of NaOH).

The sample was analyzed by HPLC. The yield, calculated based on the total peak area, is 5%. TDS-GC-MS confirmed the structure of the ester.

Discussion of Examples 12-22

These examples show that BMSC has much better reactivity than DPC or DMC in the preparation of esters, either in the solution or melt methods. For the preparation of esters from benzoic acid, the examples resulting in a white precipitate had the highest yields (examples 16 & 18). However the melt method gave the best yield of all (example 12). These results indicate that reaction to form the ester may be advantageously promoted through the use of a catalyst and somewhat elevated temperatures. Without wishing to be bound by a particular mechanism, the inventors believe that the presence of a catalyst and the use of somewhat elevated temperatures in the preparation of esters is particularly beneficial due to the quenching effects of the acidic reactant and due to the need to drive the decarboxylation reaction of the anhydride intermediate to form the final ester product.

The invention claimed is:

1. A method for forming a monomeric carbonate comprising combining a monofunctional alcohol or a difunctional diol with an ester-substituted diaryl carbonate to form a reaction mixture, and allowing the reaction mixture to react to form a monomeric carbonate.

2. The method of claim 1, wherein the monomeric carbonate has the formula:

$$R_1O—C(O)—OR_2$$

wherein $R_1$ and $R_2$ are each independently selected from the group consisting of optionally-substituted linear or branched alkyl, alkene, cycloalkyl, cycloalkenyl, aryl, heteroatom-containing aryl, and aralkyl groups, said method comprising combining monofunctional alcohols $HOR_1$ and $HOR_2$ with an ester-substituted diaryl carbonate to form the reaction mixture.

3. The method of claim 1, wherein the monomeric carbonate has the formula:

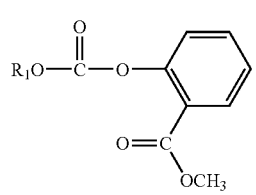

wherein $R_1$ is selected from the group consisting of optionally-substituted linear or branched alkyl, alkene, cycloalkyl, cycloalkenyl, aryl, heteroatom-containing aryl, and aralkyl groups, said method comprising combining HOR$_1$ with bismethylsalicylcarbonate to form the reaction mixture.

4. The method of claim 1, wherein the monomeric carbonate has the formula:

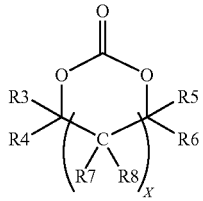

wherein:
R$_3$, R$_4$, R$_5$, and R$_6$ are each independently selected from the group consisting of hydrogen, optionally-substituted linear or branched alkyl, alkene, cycloalkyl, cycloalkenyl, aryl, heteroatom-containing aryl, and aralkyl groups, or R$_3$ or R$_4$ in combination with R$_5$ or R$_6$ forms a ring structure, X is 0 or 1 and wherein when X is 0, combinations of R$_3$ or R$_4$ and R$_5$ or R$_6$ may be absent to form a double bond, and when X is 1, R$_7$ and R$_8$ are each independently selected from the group consisting of hydrogen, optionally-substituted linear or branched alkyl, alkene, cycloalkyl, cycloalkenyl, aryl, heteroatom-containing aryl, and aralkyl groups, or combinations of R$_7$ or R$_8$ with R$_3$, R$_4$, R$_5$, or R$_6$ may also be absent to form a double bond, the method comprising combining an ester-substituted diaryl carbonate with a diol compound of structure HOR$_3$R$_4$C—(CR$_7$R$_8$)$_X$—CR$_5$R$_6$OH to form the reaction mixture.

5. The method of claim 1, wherein the ester-substituted diaryl carbonate is bismethyl salicyl carbonate.

6. The method of claim 1, wherein the reaction is performed at a temperature of less than 180° C.

7. The method of claim 6, wherein the reaction is performed at a temperature of less than 140° C.

8. The method of claim 1, wherein the reaction is performed for a period of 24 hours or less.

9. The method of claim 8, wherein the reaction is performed for a period of one hour or less.

10. The method of claim 1, wherein the reaction is performed in the presence of a catalyst, wherein the catalyst is present in an amount of $1\times10^{-6}$ to 10 mole catalyst per mole of ester-substituted carbonate.

11. The method of claim 1, wherein the reaction is performed in the absence of catalyst.

12. A composition comprising a monomeric carbonate and a detectable amount of residual ester-substituted diaryl carbonate or the corresponding ester-substituted phenolic byproduct, wherein the monomeric carbonate is a linear carbonate and has the formula:

R$_1$O—C(O)—OR$_2$ wherein R$_1$ and R$_2$ are each independently selected from the group consisting of optionally-substituted linear or branched alkyl, alkene, cycloalkyl, cycloalkenyl, aryl, heteroatom-containing aryl, and aralkyl groups, or wherein the monomeric compound is a cyclic carbonate and has the formula:

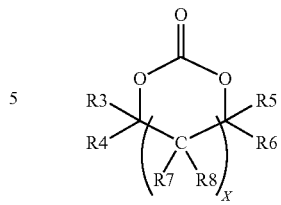

wherein:
R$_3$, R$_4$, R$_5$, and R$_6$ are each independently selected from the group consisting of hydrogen, optionally-substituted linear or branched alkyl, alkene, cycloalkyl, cycloalkenyl, aryl, heteroatom-containing aryl, and aralkyl groups, or R$_3$ or R$_4$ in combination with R$_5$ or R$_6$ forms a ring structure, X is 0 or 1 and wherein when X is 0, combinations of R$_3$ or R$_4$ and R$_5$ or R$_6$ may be absent to form a double bond, and when X is 1, R$_7$ and R$_8$ are each independently selected from the group consisting of hydrogen, optionally-substituted linear or branched alkyl, alkene, cycloalkyl, cycloalkenyl, aryl, heteroatom-containing aryl, and aralkyl groups, or combinations of R$_7$ or R$_8$ with R$_3$, R$_4$, R$_5$, or R$_6$ may also be absent to form a double bond.

13. The composition of claim 12, wherein the ester-substituted diaryl carbonate is bismethyl salicyl carbonate and the corresponding ester-substituted phenolic byproduct is methyl salicylate.

14. A method of forming a monomeric activated ester compound of the formula:

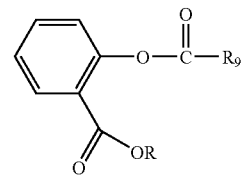

wherein R is an alkyl group, phenyl group, or a benzyl group, and R$_9$ is selected from the group consisting of optionally-substituted linear or branched alkyl, alkene, cycloalkyl, cycloalkenyl, aryl, heteroatom-containing aryl, and aralkyl groups, said method comprising reacting an ester-substituted diaryl carbonate with a compound of the formula:

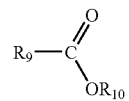

wherein R$_9$ is described above and R$_{10}$ is selected from the group consisting of hydrogen, and optionally-substituted linear or branched alkyl, alkene, cycloalkyl, cycloalkenyl, aryl, heteroatom-containing aryl, and aralkyl groups, thereby forming the compound.

15. The method of claim 14, wherein R is a methyl group and the ester-substituted diaryl carbonate is bismethyl salicyl carbonate.

16. The method of claim 14, wherein the reaction is performed at a temperature of less than 180° C.

17. The method of claim 16, wherein the reaction is performed at a temperature of less than 140° C.

18. The method of claim 14, wherein the reaction is performed for a period of 24 hours or less.

19. The method of claim 14, wherein the reaction is performed for a period of one hour or less.

20. The method of claim 14, wherein the reaction is performed in the presence of a catalyst, wherein the catalyst is present in an amount of $1\times10^{-6}$ to 10 mole catalyst per mole of ester-substituted carbonate.

21. The method of claim 14, wherein the reaction is performed in the absence of catalyst.

22. The method of claim 14, wherein $R_{10}$ is hydrogen.

23. A method of forming a monomeric ester compound of the formula:

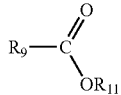

wherein $R_9$ and $R_{11}$ are the same or different and each are independently selected from the group consisting of optionally-substituted linear or branched alkyl, alkene, cycloalkyl, cycloalkenyl, aryl, heteroatom-containing aryl, and aralkyl groups, said method comprising reacting the activated ester compound prepared in claim 14 with an alcohol of structure:

$R_{11}$—OH thereby forming the monomeric ester compound.

24. A composition comprising a monomeric ester compound and a detectable amount of residual ester-substituted diaryl carbonate or the corresponding ester-substituted phenolic byproduct, wherein the monomeric ester compound has the formula:

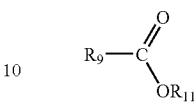

wherein $R_9$ and $R_{11}$ are the same or different and each are independently selected from the group consisting of optionally-substituted linear or branched alkyl, alkene, cycloalkyl, cycloalkenyl, aryl, heteroatom-containing aryl, and aralkyl groups.

25. The composition of claim 24, wherein the ester-substituted diaryl carbonate is bismethyl salicyl carbonate and the corresponding ester-substituted phenolic byproduct is methyl salicylate.

26. A method of forming a cyclic monomeric ester compound comprising reacting an ester-substituted diaryl carbonate with a compound comprising an alcohol group and either an ester group or a carboxylic acid group, thereby forming the cyclic monomeric ester compound.

* * * * *